(12) United States Patent
Reeves et al.

(10) Patent No.: US 7,660,451 B2
(45) Date of Patent: Feb. 9, 2010

(54) SYSTEM, METHOD AND APPARATUS FOR SMALL PULMONARY NODULE COMPUTER AIDED DIAGNOSIS FROM COMPUTED TOMOGRAPHY SCANS

(75) Inventors: Anthony P. Reeves, Ithaca, NY (US); David Yankelevitz, Brooklyn, NY (US); Claudia Henshke, New York, NY (US); Antoni Chan, Fort Worth, TX (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 12/074,211

(22) Filed: Feb. 29, 2008

(65) Prior Publication Data
US 2008/0187204 A1 Aug. 7, 2008

Related U.S. Application Data

(62) Division of application No. 10/245,782, filed on Sep. 16, 2002, now abandoned.

(60) Provisional application No. 60/322,038, filed on Sep. 14, 2001.

(51) Int. Cl.
*G06K 9/62* (2006.01)
(52) U.S. Cl. ............... 382/131; 382/215; 382/216; 382/217; 382/291
(58) Field of Classification Search ............. 382/103, 382/128–132, 173, 181, 199, 203, 209, 215, 382/216, 217, 218, 219, 257, 265, 291
See application file for complete search history.

(56) References Cited

U.S. PATENT DOCUMENTS 3,757,299 A * 9/1973 Perry ............... 382/128

4,720,870 A * 1/1988 Billiotte et al. ............. 382/145
5,228,443 A 7/1993 Tatar
5,283,837 A 2/1994 Wood (Continued)

FOREIGN PATENT DOCUMENTS

WO 01-78005 10/2001

OTHER PUBLICATIONS

Sato et al., "Tissue classification based on 3D local intensity structures for volume rendering", Apr.-Jun. 2000, Visualization and Computer Graphics, IEEE Transactions on, vol. 6, Issue 2, pp. 160-180.*

(Continued)

*Primary Examiner*—Brian P Werner
*Assistant Examiner*—Anthony Mackowey
(74) *Attorney, Agent, or Firm*—Hoffmann & Baron, LLP

(57) ABSTRACT

The present invention is directed to diagnostic imaging of small pulmonary nodules. There are two main stages in the evaluation of pulmonary nodules from Computed Tomography (CT) scans: detection, in which the locations of possible nodules are identified, and characterization, in which a nodule is represented by measured features that may be used to evaluate the probability that the nodule is cancer. Currently, the most useful prediction feature is growth rate, which requires the comparison of size estimates from two CT scans recorded at different times. The present invention includes methods for detection and feature extraction for size characterization. The invention focuses the analysis of small pulmonary nodules that are less than 1 centimeter in size, but is also suitable for larger nodules as well.

33 Claims, 26 Drawing Sheets

U.S. PATENT DOCUMENTS

| | | | | |
|---|---|---|---|---|
| 5,289,374 | A | | 2/1994 | Doi et al. |
| 5,291,560 | A | * | 3/1994 | Daugman .................... 382/117 |
| 5,351,067 | A | | 9/1994 | Lumelsky et al. |
| 5,531,520 | A | * | 7/1996 | Grimson et al. ............. 382/131 |
| 5,666,434 | A | | 9/1997 | Nishikawa et al. |
| 5,712,926 | A | | 1/1998 | Eberhard et al. |
| 5,802,135 | A | * | 9/1998 | Wohlrab ........................ 378/4 |
| 5,825,936 | A | | 10/1998 | Clarke et al. |
| 5,877,771 | A | | 3/1999 | Drebin et al. |
| 6,078,680 | A | * | 6/2000 | Yoshida et al. .............. 382/128 |
| 6,112,112 | A | * | 8/2000 | Gilhuijs et al. .............. 600/425 |
| 6,138,045 | A | * | 10/2000 | Kupinski et al. ............ 600/425 |
| 6,185,320 | B1 | * | 2/2001 | Bick et al. ................... 382/132 |
| 6,205,350 | B1 | | 3/2001 | Lorenz et al. |
| 6,229,907 | B1 | * | 5/2001 | Okano et al. ................. 382/117 |
| 6,243,494 | B1 | * | 6/2001 | Sun et al. ..................... 382/216 |
| 6,246,784 | B1 | * | 6/2001 | Summers et al. ............ 382/128 |
| 6,470,092 | B1 | * | 10/2002 | Li et al. ....................... 382/132 |
| 6,754,374 | B1 | * | 6/2004 | Miller et al. ................. 382/128 |
| 6,816,607 | B2 | * | 11/2004 | O'Donnell et al. .......... 382/131 |
| 6,993,174 | B2 | * | 1/2006 | Fan et al. ..................... 382/131 |
| 7,272,250 | B2 | * | 9/2007 | Schneider et al. ........... 382/128 |

OTHER PUBLICATIONS

Staib et al., "Boundary finding with parametrically deformable models", Nov. 1992, Pattern Analysis and Machine Intelligence, IEEE Transactions on, vol. 14, No. 11, pp. 1061-1075.*

Yamashita et al., "Small Peripheral Lung Carcinoma Evaluated with Incremental Dynamic CT: Radiologic-Pathologic Correlation", Radiology 1995, vol. 196, No. 2, pp. 401-408.*

Raptis et al., "Growing region technique in the detection of autonomous structures within x-ray radiographs", Nov. 1997, IEEE, Nuclear Science Symposium, vol. 2, pp. 1576-1580.*

Author: A. Akanuma; Title: "Clinical method to estimate time of origin and maximum volume of malignant tumors"; *Radiation Medicine*, 1(1):89-104; Date of Publication: Jan.-Mar. 1983; Place of Publication: Japan.

Author: E. Arana, P. Delicado, and L. Marti-Bonmati,; Title: "Validation procedures in radiologic diagnostic models"; Neural network and logistic regression. *Investigative Radiology*. 34(10):636-642; Date of Publication: Oct. 1999; Place of Publication: Spain.

Author: S. G. Armato, III, M. L. Giger, K. Ashizawa, and H. MacMahon; Title: "Automated lung segmentation in digital lateral chest radiographs"; *Medical Physics*, 25(8):1507-1520; Date of Publication: Aug. 1998; Place of Publication: U.S.

Author: S. G. Armato, III, M. L. Giger, C. J. Moran, J. T. Blackburn, K. Doi, and H. MacMahon; Title: "Computerized detection of pulmonary nodules on CT scans"; *Radiographics*, 19(5):1303-1311; Date of Publication: Sep.-Oct. 1999; Place of Publication: U.S.

Author: P. J. Besl and R. C. Jain; Title: "Invariant surface characteristics for 3D object recognition in range images"; *Computer Vision, Graphics, and Image Processing*, 33(1):33-80; Date of Publication: Jan. 1986; Place of Publication: U.S.

Author: R. N. Bracewell and S. J. Wernecke; Title: "Image reconstruction over a finite field of view"; *Journal of the Optical Society of America*, 65:1342-1346; Date of Publication: 1975; Place of Publication: U.S.

Author: M.S. Brown, M. F. McNitt-Gray, N. J. Mankovich, J. G. Goldin, J. Hiller, L. S. Wilson, and D. R. Aberle; Title: "Method for segmenting chest CT image data using an anatomical model: Preliminary results"; *IEEE Transactions on Medical Imaging*, 16(6):828-839; Date of Publication: Dec. 1997; Place of Publication: U.S.

Author: M. J. Carreira, D. Cabello, M. G. Penedo, and A. Mosquera; Title: "Computer-aided diganoses: Automatic detection of lung nodules"; *Medical Physics*, 25(10):1998-2006; Date of Publication: Oct. 1998; Place of Publication: Spain.

Author: J. Collins and E. J. Stern; Title: "Ground-glass opacity at CT: the ABCs"; *AJR American Journal of Roentgenology*; 169(2):355-367; Date of Publication: Aug. 1997; Place of Publication: U.S.

Author: V. P. Collins, R. K. Loeffler, and H. Tivey; Title: "Observations on growth rates of human tumors"; *American Journal of Roentgenology*, 76:988-1000; Date of Publication: 1956; Place of Publication: U.S.

Author: A. M. Cormack.; Title: "Representation of a function by its line integrals with some radiological applications"; *Journal of Applied Physics*, 34:2722-2727; Date of Publication: 1963; Place of Publication: U.S.

Author: A. M. Cormack.; Title: "Representation of a function by its line integrals with some radiological applications II"; *Journal of Applied* Physics, 34:2908-2913; Date of Publication: 1964; Place of Publication: U.S.

Author: P. Croisille, M. Souto, M. Cova, S. Wood, Y. Afework, J. E. Kuhlman, and E. A. Zerhouni; Title: "Pulmonary nodules: Improved detection with vascular segmentation and extraction with spiral CT"; Work in progress. *Radiology*, 197(2):397-401; Date of Publication: Nov. 1995; Place of Publication: U.S.

Author: S. Dholakia and D. C. Rappaport; Title: "The solitary pulmonary nodule. Is it malignant or benign?"; *Postgraduate Medicine*, 99(2):246-250; Date of Publication: Feb. 1996; Place of Publication: U.S.

Author: C. E. Engeler, J. H. Tashjian, S. W. Trenkner, and J. W. Walsh; Title: "Ground-glass opacity of the lung parenchyma: a guide to analysis with high-resolution CT"; *AJR American Journal of Roentgenology*, 160(2):249-251; Date of Publication: Feb. 1993; Place of Publication: U.S.

Author: B. J. Flehinger, M. Kimmel, T. Polyak, and M. R. Melamed; Title: "Screening for lung cancer"; The Mayo Lung Project revisited. *Cancer*, 72(5):1573-1580; Date of Publication: Sep. 1, 1993; Place of Publication: U.S.

Author: R. S. Fontana, D. R. Sanderson, L. B. Woolner, W. F. Taylor, W. E. Miller, J. R. Muhm, P. E. Bernatz, W. S. Payne, P. C. Pairolero, and E. J. Bergstralh; Title: "Screening for lung cancer"; A critique of the Mayo Lung Project. *Cancer*, 67(4 (suppl.)):1155-1164; Date of Publication: Feb. 15, 1991; Place of Publication: U.S.

Author: A. Van Gelder and J. Wilhelms; Title: "Topological considerations in isosurface generation"; *ACM Transactions on Graphics*, 13(4):337-375; Date of Publication: Oct. 1994; Place of Publication: U.S.

Author: M. L. Giger, K. T. Bae, and H. MacMahon; Title: "Computerized detection of pulmonary nodules in computed tomography images"; *Investigative Radiology*, 29(4):459-465; Date of Publication: Apr. 1994; Place of Publication: U.S.

Author: M. L. Giger, K. Doi, and H. MacMahon; Title: "Image feature analysis and computer-aided diagnosis in digital radiography. 3. Automated detection of nodules in peripheral lung fields"; *Medical Physics*, 15(2):158-166; Date of Publication: Mar.-Apr. 1988; Place of Publication: U.S.

Author: J. W. Green and C. C. Lushbaugh; Title: "Histopathological study of the mode of inhibition of cellular proliferation by urethane"; *Cancer Research*, 9:199-209; Date of Publication: 1949; Place of Publication: U.S.

Author: Gurney, Jud W.; Title: "Determining the likelihood of malignancy in solitary pulmonary nodules with Bayesian analysis"; Part 1. Theory. *Radiology*, 186(2):405-413; Date of Publication: Feb. 1993; Place of Publication: U.S.

Author: J. A. Hanley and B. J. McNeil; Title: "The meaning and use of the area under a receiver operating characteristic (ROC) curve"; *Radiology*. 143(1):29-36; Date of Publication: Apr. 1982; Place of Publication: Canada.

Author: C.I. Henschke, D.I. McCauley, D.F. Yankelevitz, D. P. Naidich, G. McGuinness, O. S. Miettinen, D. M. Libby, M. W. Pasmantier, J. Koizumi, N. K. Altorki, and J. P. Smith; Title: "Early Lung Cancer Action Project: overall design and findings from baseline screening;" *Lancet*, 354(9173):99-105; Date of Publication: Jul. 1999; Place of Publication: U.S.

Author: C. J. Herold, A. A. Bankier, and D. Fleischmann; Title: "Lung metastases"; *European Radiology*, 6(5):596-606; Date of Publication: 1996; Place of Publication: Austria.

Author: G. N. Hounsfield; Title: "Computerized transverse axial scanning (tomography). 1. Description of system"; *British Journal of Radiology*, 46(552):1016-1022; Date of Publication: Dec. 1973; Place of Publication: England.

Author: G. N. Hounsfield; Title: "Computed medical imaging": Nobel lecture, Dec. 8, 1979. *Journal of Computer Assisted Tomography*, 4(5):665-674; Date of Publication: Oct. 1980; Place of Publication: England.

Author: Z. Huo, M. L. Giger, C. J. Vyborny, U. Bick, P. Lu, D. E. Wolverton, and R. A. Schmidt; Title: "Analysis of spiculation in the computerized classification of mammographic masses"; *Medical Physics*, 22(10):1569-1579; Date of Publication: Oct. 1995; Place of Publication: U.S.

Author: Z. Huo, M. L. Giger, C. J. Vyborny, D. E. Wolverton, R. A. Schmidt, and K. Doi; Title: "Automated computerized classification of malignant and benign masses on digitized mammograms"; *Academic Radiology*, 5(3):155-168; Date of Publication: Mar. 1998; Place of Publication: U.S.

Author: S. Itoh, M. Ikeda, T. Isomura, T. Endo, K. Yamakawa, K. Itoh, S. Naganawa, K. Maruyama, and T. Ishigaki; Title: "Screening helical CT for mass screening of lung cancer: application of low-dose and single-breath-hold scanning"; *Radiation Medicine*, 16(2):75-83; Date of Publication: Mar.-Apr. 1998; Place of Publication: Japan.

Author: L. R. Kaiser and J. B. Shrager; Title: "Video-assisted thoracic surgery: the current state of the art"1*AJR American Journal of Roentgenology*, 99(2):246-250; Date of Publication: Feb. 1996; Place of Publication: U.S.

Author: W. A. Kalender; Title: "Technical foundations of spiral CT"; *Seminars in Ultrasound, CT, and MRI*, 15(2):81-89; Date of Publication: Apr. 1994; Place of Publication: Germany.

Author: W. A. Kalender; "Thin-section three-dimensional spiral CT: is isotropic imaging possible?"; *Radiology*, 197(3):578-580; Date of Publication: Dec. 1995; Place of Publication: Germany.

Author: W. A. Kalender, W. A. Seissle, E. Klotz, and P. Vock; Title: "Spiral volumetric CT with single breath-hold technique continuous transport and continuous scanner rotation"; *Radiology*, 176(1):181-183; Date of Publication: Jul. 1990; Place of Publication:Switzerland.

Author: M. Kaneko, K. Eguchi, H. Ohmatsu, R. Kakinuma, T. Naruke, K. Suemasu, and N. Moriyma; Title: "Peripheral lung cancer: screening and detection with low-dose spiral CT versus radiograpjy"; *Radiology*, 201(3):798-802; Date of Publication: Dec. 1996; Place of Publication: Japan.

Author: Y. Kawata, N. Hiki, H. Ohmatsu, K. Eguchi, and N. Moriyama; Title: "Shape analysis of pulmonary nodules based on thin section CT images"; SPIE *Proceedings*. 3034:964-974; Date of Publication: Feb. 1997; Place of Publication: Japan.

Author: J. H. Kim, J. G. Im, M. C. Han, B. G. Min, and C. W. Lee; Title: "Improved visualization of simulated nodules by adaptive enhancement of digital chest radiography"; *Academic Radiology*, 1(2):93-99; Date of Publication: Oct. 1994; Place of Publication: South Korea.

Author: T. Kobayashi, X.-W. Xu, H. MacMahon, C. E. Metz, and K. Doi; Title: "Effect of a computer-aided diagnosis scheme on radiologists' performance in detection of lung nodules on radiographs"; *Radiology*, 199(3):843-848; Date of Publication: Jun. 1996; Place of Publication: U.S.

Author: A. K. Laird; Title: "Dynamics of tumor growth: Comparison of growth rates and extrapolation of growth curve to one cell"; *British Journal of Cancer*, 19:278-291; Date of Publication: 1965; Place of Publication: U.S.

Author: S.H. Landis, T. Murray, S. Bolden, and P. A. Wingo; Title: "Cancer statistics, 1999";. *CA: Cancer Journal for Clinicians*, 49(1):8-31; Date of Publication: Jan.-Feb. 1999; Place of Publication: U.S.

Author: G. A. Lillington; Title: "Management of solitary pulmonary nodules"; *Postgraduate Medicine*, 101(3):145-150; Date of Publication: Mar. 1997; Place of Publication: U.S.

Author: W. E. Lorensen and H. E. Cline; Title: "Marching cubes: A high resolution 3D surface construction algorithm"; *Computer Graphics*, 21(4):163-169; Date of Publication: Jul. 1987; Place of Publication: U.S.

Author: F. Mao, W. Qian, J. Gaviria, and L. P. Clarke; Title: "Fragmentary window filtering for multiscale lung nodule detection: Preliminary study"; *Academic Radiology*, 5(4):306-311; Date of Publication: Apr. 1998; Place of Publication: U.S.

Author: T. Matsumoto, H. Yoshimura, K. Doi, M. L. Giger, A. Kano, H. MacMahon, K. Abe, and S. M. Montner; Title: "Image feature analysis of false-positive diagnoses produced by automated detection of lung nodules"; *Investigative Radiology*, 27(8):587-597; Date of Publication: Aug. 1992; Place of Publication: U.S.

Author: M. F. McNitt-Gray, E. M. Hart, N. Wyckoff, J. W. Sayre, J. G. Goldin, and D. R. Aberle; Title: "A pattern classification approach to characterizing solitary pulmonary nodules imaged on high resolution CT: Preliminary results"; *Medical Physics*, 26(6):880-888; Date of Publication: Jun. 1999; Place of Publication: U.S.

Author: M.R. Melamed, B. J. Flehinger, M. B. Zaman, R. T. Heelan, W. A. Perchick, and N. Martini; Title: "Screening for early lung cancer. Results of the Memorial Sloan-Kettering study in New York"; *Chest*, 86(1):44-53; Date of Publication: Jul. 1984; Place of Publication: U.S.

Author: S. Mitruka, R. J. Landreneau, M. J. Mack, L. S. Fetterman, J. Gammie, S. Bartley, S. R. Sutherland, C. M. Bowers, R. J. Keenan RJ, P. F. Ferson, and R. J. Weyant; Title: "Diagnosing the indeterminate pulmonary nodule: percutaneous biopsy versus thoracoscopy"; *Surgery*, 118(4):676-684; Date of Publication: Oct. 1995; Place of Publication: U.S.

Author: O. Monga, R. Deriche, and J.-M. Rocchisani; Title: "3D edge detection using recursive filtering: Application to scanner images"; *Computer Vision, Graphics, and Image Processing: Image Understanding*, 53(1)76-87; Date of Publication: Jan. 1991; Place of Publication: France.

Author: H. Nathan; Title: "Management of solitary pulmonary nodules. An organized approach based on growth rate and statistics"; *JAMA*, 227(10):1141-1144; Date of Publication: Mar. 1974; Place of Publication: U.S.

Author: M. H. Nathan, V. P. Collins, and R. A. Adams; Title: "Differentiation of benign and malignant pulmonary nodules by growth rate"; *Radiology*, 79:221-231; Date of Publication: 1962; Place of Publication: U.S.

Author: R. Pearl and L. J. Reed; Title: "On the rate of growth of the population of the United States since 1790 and its mathematical presentation"; *Proceedings of the National Academy of Sciences*, 6:275-285; Date of Publication: 1920; Place of Publication: U.S.

Author: J. Peiss, M. Verlande, W. Ameling, and R. W. Guenther; Title: "Classification of lung tumors on chest radiographs by fractal texture analysis"; *Investigative Radiology*, 31(10):625-629; Date of Publication: Oct. 1996; Place of Publication: Germany.

Author: M. G. Penedo, M. J. Carreira, A. Mosquera, and D. Cabello; Title: "Computer-aided diagnosis: A neural-based approach to lung nodule detection"; *IEEE Transactions on Medical Imaging*, 17(6):872-880; Date of Publication: Dec. 1998; Place of Publication: Spain.

Author: R. J. Prokop and A. P. Reeves; Title: "A survey of moment-based techniques for unoccluded object representation and recognition"; *CVGIP: Graphical Models and Image Processing*, 54(5):438-360; Date of Publication: Sep. 1992; Place of Publication: U.S.

Author: R. D. Pugatch; Title: "Radiologic evaluation in chest malignancies. A review of imaging modalities"; *Chest*, 107(6 (suppl. )):294S-297S; Date Publication: Jun. 1995; Place of Publication: U.S.

Author: A. P. Reeves, W. J. Kostis, D. F. Yankelevitz, and C. I. Henschke; Title: "Three-dimensional shape characterization of solitary pulmonary nodules from helical CT scans"; In H. U. Lemke, M. W. Vannier, K. Inamura, and A. G. Farman, editors, *Proceedings of Computer Assisted Radiology and Surgery (CARS '99)*, pp. 83-87. Elsevier Science; Date of Publication: Jun. 1999; Place of Publication: U.S.

Author: A. P. Reeves, R. J. Prokop, S. E. Andrews, and F. P. Kuhl; Title: "Three-dimensional shape analysis using moments and Fourier descriptors"; *IEEE Transactions on Pattern Analysis and Machine Intelligence*, 10(6):937-943; Date of Publication: Nov. 1988; Place of Publication: U.S.

Author: A. P. Reeves and B. S. Wittner; Title: "Shape analysis of three dimensional objects using the method of moments"; In *Proceedings of 1983 IEEE Conference on Computer Vision and Patten Recognition*, pp. 20-26; Date of Publication: Jun. 1983; Place of Publication: U.S.

Author: T. W. Ridler and S. Calvard; Title: "Picture thresholding using an iterative selection method"; *IEEE Transactions on Systems, Man, and Cybernetics,* SMC-8(8):630-632; Date of Publication: Aug. 1978; Place of Publication: London.

Author: K. V. Rolston, S. Rodriguez, M. Dholakia, E. Whimbey E, and I. Raad; Title: "Pulmonary infections mimicking cancer: a retrospective; three-year review"; *Support Care Cancer;* 5(2):90-93; Date of Publication: Mar. 1997; Place of Publication: U.S.

Author: S. Sanada, K. Doi, and H. MacMahon; Title: "Image feature analysis and computer-aided diagnosis in digital radiography: automated delineation of posterior ribs in chest images"; *Medical Physics,* 18(5):964-971; Date of Publication: Sep.-Oct. 1991; Place of Publication: U.S.

Author: M. D. Seemann, A. Staebler, T. Beinert, H. Dienemann, B. Obst, M. Matzko, C. Pistitsch, and M. F. Reiser; Title: "Usefulness of morphological characteristics for the differentiation of benign from malignant solitary pulmonary lesions using HRCT;" *European Radiology,* 9(3):409-417; Date of Publication: 1999; Place of Publication: Germany.

Author: R.. Shah, S. Sabanathan, J. Richardson, A. J. Mearns, and C. Goulden; Title "Results of surgical treatment of stage I and II lung cancer"; *Journal of Cardiovascular Surgery,* 37(2):169-172; Date of Publication: Apr. 1996; Place of Publication: United Kingdom.

Author: R. H. Sherrier, C. Chiles, W. E. Wilkinson, G. A. Johnson, and C. E. Ravin; Title: "Effects of image processing on nodule detection rates in digitized chest radiographs: ROC study of observer performance"; *Radiology,* 166(2):447-450; Date of Publication: Feb. 1998; Place of Publication: U.S.

Author: S. Sone, S. Takashima, F. Li, Z. Yang, T. Honda, Y. Maruyama, M. Hasegawa, T. Yamanda, K. Kubo, K. Hanamura, and K. Asakura; Title: "Mass screening for lung cancer with mobile spiral computed tomography scanner"; *Lancet,* 351(9111):1242-1245; Date of Publication: Apr. 1998; Place of Publication: Japan.

Author: M. Sonka, G. Sundararmoorthy, and E. A. Hoffman; Title: "Knowledge-based segmentation of intrathoracic airways from multidimensional high resolution CT images"; *SPIE,* 2168:73-85; Date of Publication: Aug. 1994; Place of Publication: U.S.

Author: J. S. Spratt, J. S. Meyer, and J. A. Spratt; Title: "Rates of growth of human solid neoplasms: Part 1"; *Journal of Surgical Oncology,* 60(2):137-146; Date of Publication: Oct. 1995; Place of Publication: U.S.

Author: S. J. Swensen, J. R. Jett, W. S. Payne, R. W. Viggiano, P. C. Pairolero, and V. F. Trastek; Title: "An integrated approach to evaluation of the solitary pulmonary nodule"; *Mayo Clinic Proceedings,* 65(2):173-186; Date of Publication: Feb. 1990; Place of Publication: U.S.

Author: S. J. Swensen, M. D. Silverstein, D. M. Ilstrup, C. D. Schleck, and E. S. Edell; Title: "The probability of malignancy in solitary pulmonary nodules. Application to small radiologically indeterminate nodules"; *Archives of Internal Medicine,* 157(8):849-855; Date of Publication: Apr. 1997; Place of Publication: U.S.

Author: S. Toshioka, K. Kanazawa, N. Niki, H. Satoh, H. Ohmatsu, K. Eguchi, and N. Moriyama; Title: "Computer aided diagnosis system for lung cancer based on helical CT images"; *SPIE Proceedings,* 3034:975-984; Date of Publication: Feb. 1997; Place of Publication: Japan.

Author: J. D. Urschel; Title: "Surgical treatment of peripheral small cell lung cancer"; *Chest Surg Clin N Am,* 7(1):95-103; Date of Publication: Feb. 1997; Place of Publication: U.S.

Author: K. Usuda, Y. Saito, M. Sagawa, M. Sato, K. Kanma, S. Takahashi, C. Endo, Y. Chen, A. Sakurada, and S. Fujimura; Title: "Tumor doubling time and prognostic assessment of patients with primary lung cancer"; *Cancer,* 74(8):2239-2244; Date of Publication: Oct. 1994; Place of Publication: Japan.

Author: N. F. Vittitoe, J. A. Baker, and C. E. Floyd; Title: "Fractal texture analysis in computer-aided diagnosis of solitary pulmonary nodules"; *Academic Radiology,* 4(2):96-101; Date of Publication: Feb. 1997; Place of Publication: U.S.

Author: P. Vock, M. Soucek, M. Daepp, and W. A. Kalender; Title: "Lung: spiral volumetric CT with single-breath-hold technique"; *Radiology,* 176(3):864-867; Date of Publication: Sep. 1990; Place of Publication: Switzerland.

Author: W. Weiss; Title: "Implications of tumor growth rate for the natural history of lung cancer"; *Journal of Occupational Medicine,* 26(5):345-352; Date of Publication: May 1984; Place of Publication: U.S.

Author: S. A. Wood, E. A. Zerhouni, J. D. Hoford, E. A. Hoffman, and W. Mitzner; Title: "Measurement of three-dimensional lung tree structures by using computed tomography"; *Journal of Applied Physiology,* 79(5):1687-97; Date of Publication: Nov. 1995; Place of Publication: U.S.

Author: X.-W. Xu and K. Doi; Title: "Image feature analysis for computer-aided diagnosis: Accurate determination of ribcage boundary in chest radiographs"; *Medical Physics,* 22(5):617-626; Date of Publication: May 1995; Place of Publication: U.S.

Author: X.-W. Xu and K. Doi; Title: Image feature analysis for computer-aided diagnosis: Detection of right and left hemidiaphragm edges and delineation of lung field in chest radiographs *Medical Physics,* 23(9):1613-1624; Date of Publication: Sep. 1996; Place of Publication: U.S.

Author: X.-W. Xu, K. Doi, T. Kobayashi, H. MacMahon, and M. L. Giger; Title: "Development of an improved CAD scheme for automated detection of lung nodules in digital chest images"; *Medical Physics,* 24(9):1395-1403; Date of Publication: Sep. 1997; Place of Publication: U.S.

Author: S. Yamamoto, I. Tanaka, M. Senda, Y. Tateno, T. Iinuma, T. Matsumoto, and M. Matsumoto; Title: "Image processing for computer-aided diagnosis of lung cancer by CT (LSCT)"; *Systems and Computers in Japan.* 25(2):67-80; Date of Publication: Feb. 1994; Place of Publication: Japan.

Author:D. F. Yankelevitz, C. I. Henschke, J. H. Koizumi, N. K. Altorki, and D. Libby; Title: "CT-guided transthoracic needle biopsy of small solitary pulmonary nodules"; *Clinical Imaging,* 21(2):107-10; Date of Publication: Mar.-Apr. 1997; Place of Publication: U.S.

Author: H. Yoshimura, M. L. Giger, K. Doi, H. MacMahon, and S. M. Montner; Title: "Computerized scheme for the detection of pulmonary nodules: A nonlinear filtering technique"; *Investigative Radiology,* 27(2):124-129; Date of Publication: Feb. 1992; Place of Publication: U.S.

Author: T. Fleiter, E.M. Merkle, A.J. Aschoff, G. Lang, M. Stein, J. Gorich, F. Liewald, N. Rilinger, and R. Sokiranski; Title: "Comparison of real-time virtual and fiberoptic bronchoscopy in patients with bronchial carcinoma: opportunities and limitations"; *American Journal of Roentgenology,* 169(2):1591-1595; Date of Publication: Dec. 1997; Place of Publication: Germany.

Author: M. L. Giger, K.T. Bae, and H. MacMahon; Title: "Image processing and computer-aided diagnosis"; *Radiologic Clinics of North America,* 34(3):565-596; Date of Publication: May 1996; Place of Publication: U.S.

Author: P. A. Heng, P. F. Fung, T. T. Wong, Y. H. Siu, and H. Sun; Title: "Interactive navigation and bronchial tube tracking in virtual bronchoscopy"; *Studies in Health Technology and Informatics,* 62:130-133; Date of Publication: 1999; Place of Publication: Hong Kong.

Author: W. J. Kostis, A. P. Reeves, D. F. Yankelvitz, and C. I. Henschke; Title: "Three-dimensional segmentation of solitary pulmonary nodules from helical CT scans"; In H. U. Lemke, M. W. Vannier, K. Inamura, and A. G. Farman, editors, *Proceedings of Computer Assisted Radiology and Surgery (CARS '99),* pp. 203-207. Elsevier Science: Date of Publication: Jun. 1999; Place of Publication: U.S.

Author: F. Maes, A. Collingnon, D. Vandermeulen, G. Marchal, and P. Suetens. Title: "Multimodality image registration by maximization of mutual information"; *IEEE Transactions on Medical Imaging,* 16(2):187-198; Date of Publication: Apr. 1997; Place of Publication: Belgium.

Author: W. Park, E. A. Hoffman, and M. Sonka; Title: "Segmentation of intrathoracic airway trees: A fuzzy logic approach"; *IEEE Transactions on Medical Imaging,* 17(4):489-197; Date of Publication: Aug. 1998; Place of Publication: U.S.

Author: A. P. Reeves and W. J. Kostis; "Computer-aided diagnosis for lung cancer"; *Radiologic Clinics of North America,* 38(3):497-509; Date of Publication: May 2000; Place of Publication: U.S.

Author: R. M. Summers, D. H. Feng, S. M. Holland, M. C. Sneller, and J. H. Shelhamer; Title: "Virtual bronchoscopy: Segmentation method for real-time display"; *Radiology*, 200(3):857-862; Date of Publication: Sep. 1996; Place of Publication: U.S.

Author: J. K. Udupa; Title: "Three-dimensional visualization and analysis methodologies: a current perspective"; *Radiographics*, 19(3):783-806; Date of Publication: May-Jun. 1999; Place of Publication: U.S.

Author: W. M. Wells, III, P. Viola, H. Atsumi, S. Nakajima, and R. Kikinis; Title: "Multi-modal volume registration by maximization of mutual information"; *Medical Image Analysis*, 1(1):35-51; Date of Publication: Mar. 1996; Place of Publication: U.S.

Author: D. F. Yankelevitz, R. Gupta, B. Zhao, and C. I. Henscke;, Title: "Small pulmonary nodules: Evaluation with repeat CT-preliminary experience"; *Radiology*, 212(2):561-566; Date of Publication: Aug. 1999; Place of Publication: U.S.

Author: D. F. Yankelevitz, A. P. Reeves, W. J. Kostis, B. Zhao, and C. I. Henschke; Title: "Small Pulmonary Nodules: Volumetrically Determined Growth Rates Based on CT Evaluation"; Radiology, 217(1):251-256; Date of Publication: Oct. 2000; Place of Publication: U.S.

Author: A. P. Reeves and W. J. Kostis; Title: "Computer-Aided Diagnosis of Small Pulmonary Nodules"; *Seminars in Ultrasound, CT, and MRI*, 21(2):116-128; Date of Publication: Apr. 2000; Place of Publication: U.S.

Author: B. Zhao, W. J. Kostis, A. P. Reeves, D. F. Yankelevitz, and C. I. Henschke; Title: "Consistent Segmentation of Repeat CT Scans for Growth Assessment in Pulmonary Nodules"; Proceedings of the SPIE, Medical Imaging 1999, 3661:1012-1018; Date of Publication: May 1999; Place of Publication: U.S.

Author: S. Hu, E. A. Hoffman, and J.M. Reinhardt; Title: "Automatic Lung Segmentation for Accurate Quantitation of Volumetric X-Ray CT Images"; *IEEE Transactions on Medical Imaging*, vol. 20, No. 6; Date of Publication: Jun. 2001; Place of Publication: U.S.

Author: J. Hsieh; Title: "Generalized Adaptive Median Filters and their Application in Computed Tomography"; *SPIE* vol. 2298, pp. 662-669; Date of Publication: 1994; Place of Publication: U.S.

Author: J. Hsieh; Title: "Adaptive Trimmed Mean Filter for CT Imaging"; Mathematical Methods in Medical Imaging III, Proceedings of *SPIE*, vol. 2299, pp. 316-324; Date of Publication: 1994; Place of Publication: U.S.

Author: H. Soltanian-Zadeh, J.P. Windham and J. Soltanianzadeh; Title: "CT Artifact Correction: An Image Processing Approach"; Medical Imaging 1996: Image Processing, Proceedings of *SPIE*, vol. 2710, pp. 477-485; Date of Publication:1996; Place of Publication: U.S.

Author: A. P. Reeves, W. J. Kostis, D. F. Yankelevitz, C.I. Henschke; Title: "Analysis of Small Pulmonary Nodules without Explicit Segmentation of CT images"; *Radiological Society of North America—2000 Scientific Program*, vol. 217, pp. 243-244; Date of Publication: Nov. 2000; Place of Publication: U.S.

Author: Y. Lee, T., Hara, H. Fujita, S. Itoh, and T. Ishigaki; Title: "Automatic Detection of Pulmonary Nodules in Helical CT Images Based on an Improved Template-Matching Technique"; *IEEE Transactions on Medical Imaging*, vol. 20, No. 7, pp. 595-604; Date of Publication: Jul. 2001; Place of Publication: U.S.

Author: F. Maes, A. Collignon, D. Vandermeulen, G. Marchal and P. Suetens; Title: "Multimodality image registration by maximization of mutual information"; *IEEE Transactions on Medical Imaging*, vol. 16, No. 2, pp. 187-198; Date of Publication: Apr. 1997; Place of Publication: U.S.

Author: Takagi, N.; Kawata, Y., Nikvi, N.; Morit, K.; Ohmatsu, H.; Kakinuma, R.; Eguchi, K.; Kusumoto, M.; Moriyama, N.; Title: "Computerized characterization of contrast enhancement patterns for classifying pulmonary nodules"; *Image Processing, 2000. Proceedings. 2000 International Conference* on vol. 1, pp. 188-191; Date of Publication: 2000; Place of Publication: U.S.

Author: A. P. Reeves, W. J. Kostis; Title: "Computer-Aided Diagnosis of Small Pulmonary Nodules"; *Seminars in Ultrasound, CT, and MRI*, vol. 21, No. 2, pp. 116-128; Date of Publication: Apr. 2000; Place of Publication: U.S.

Author: W. J. Kostis, A. P. Reeves, D. F. Yankelevitz, C.I. Henschke; Title: "Three-dimensional segmentation of solitary pulmonary nodules from helical CT scans"; *CARS '99 Computer Assisted Radiology and Surgery: Proceedings of the 13th International Congress and Exhibition*, pp. 203-207; Date of Publication: 1999; Place of Publication: U.S.

Author: American Cancer Society; Title: "Cancer Facts & Figures 2002"; 1599 Clifton Road, NE, Atlanta, GA, 30329-4251.

Author: Claudia I. Henschke, D.P. Naidich, D.F. Yankelevitz, G. McGuinness, D.I. McCauley, J.P. Smith, D.M. Libby, M.W. Pasmantier, M. Vazquez, J. Koizumi, D. Flleder, N.K. Altorki, and O.S. Miettinen; Title: "Early Lung Cancer Action Project: Initial Findings on Repeat Screening"; Cancer Jul. 1, 2001; 92(1):153-159; Date of Publication: Jul. 1, 2001; Place of Publication: U.S.

Author: R. Kakinuma, H. Ohmatsu, M. Kaneko, K. Eguchi, K. Naruke, K. Nagai; Title: "Detection failures in spiral CT screening for lung cancer: analysis of CT findings"; Radiology, 212, pp. 61-66; Date of Publication: 1999; Place of Publication: U.S.

Author: M. Remy Jardin, F. Giraud, C-H Marquette; Title: "Pulmonary nodules: detection with thick section spiral CT versus conventional CT"; Radiology, 187(No. 2), pp. 513-520; Date of Publication: 1993; Place of Publication: U.S.

Author: S.H. Heywang-Koebrunner, B. Lommatzsch, et al.; Title: "Comparison of spiral and conventional CT in the detection of pulmonary nodules(abstract)"; Radiology, 185, 131; Date of Publication: 1992; Place of Publication: U.S.

Author: J.A. Buckley, W.W. Scott, S.S. Siegelman, et al.; Title: "Pulmonary nodules: effect of increased data sampling on detection with spiral CT and confidence in diagnosis"; Radiology, 196, pp. 395-400; Date of Publication: 1995; Place of Publication: U.S.

Author: G. Cittadini Jr., R. Conzi, and G. Motta; Title: "Spiral computed tomography in the diagnosis and staging of bronchopulmonary carcinoma"; *Chir Ital*, 47(3):13-17; Date of Publication: 1995; Place of Publication: U.S.

Author: ACR-NEMA Standards Committee. *Digital Imaging and Communications in Medicine (DICOM): Version 3.2*. Rossyln, VA; Date of Publication: 1999; Place of Publication: U.S.

Author: R. C. Gonzales and R. E. Woods; *Digital Image Processing*. Addison-Wesley, Reading, MA; Date of Publication: 1992; Place of Publication: U.S.

Author: R. Jain, R. Kasturi, and B. G. Schunck. *Machine Vision*. McGraw-Hill, New York; Date of Publication: 1995; Place of Publication: U.S.

Author: A. P. Reeves, W. J. Kostis, C. I. Henschke, B. Zhao, and D. F. Yankelevitz; Title: "Three-dimensional feature characterization of small pulmonary nodules from helical CT images"; *Radiology*, 209P:163; Date of Publication: Nov. 1998; Place of Publication: U.S.

.Author: J. Remy, M. Remy-Jardin, F. Giraud, and J. Wannebroucq; Title: "Spiral volumetric scanning and its applications in thoracic pathology"; *Rev Mal Respir* 11(1):13-27; Date of Publication: 1994; Place of Publication: U.S.

Author: S. Sasaoka. H. Takabatake, M. Mori, H. Natori, and S. Abe; Title: "Digital analysis of pulmonary nodules-potential usefulness of computer-aided diagnosis for differentiation of benign from malignant nodules"; *Nippon Kyobu Shikkan Gakkai Zasshi*, 33(5):489-496; Date of Publication: May 1995; Place of Publication: U.S.

Author: P. Chandrasekhar, L. Wolff, E. Zerhouni, and W. Mitzner; Title: "Segmentation of 3 pulmonary trees using mathematical morphology"; In P. Maragos, R. W. Schafer, and M. A. Butt, editors, *Mathematical Morphology and its Applications to Image and Signal Processing*, pp. 409-416. Kluwer Academic Press; Date of Publication: May 1996; Place of Publication: U.S.

Author: D. F. Yankelevitz, A. P. Reeves, W. J. Kostis, B. Zhao, and C. I. Henschke; Title: "Determination of malignancy in small pulmonary nodules based on volumetrically determined growth rates"; *Radiology*, 209P:375; Date of Publication: Nov. 1998; Place of Publication: U.S.

Author: S. Hu, E. A. Hoffman, and J. M. Reinhardt; Title: "Automatic Lung Segmentation for Accurate Quantitation of Volumetric X-Ray CT Images"; *IEEE Transactions on Medical Imaging*, vol. 20, No. 6; Date of Publication: Jun. 2001.

Author: J. Hsieh; Title: "Generalized Adaptive Median Filters and their Application in Computed Tomography"; *SPIE*, vol. 2298, pp. 662-669; Date of Publication: 1994; Place of Publication: U.S.

Author: Y. Lee, T., Hara, H. Fujita, S. Itoh, and T. Ishigaki; Title: "Automatic Detection of Pulmonary Nodules in Helical CT Images Based on an Improved Template-Matching Technique"; *IEEE Transactions on Medical Imaging*, vol. 20, No. 7, pp. 595-604; Date of Publication: Jul. 2001.

Author: F. Maes, A. Collingnon, D. Vandermeulen, G. Marchal and P. Suetens; Title: "Multimodality image registration by maximization of mutual information"; *IEEE Transactions on Medical Imaging*, vol. 16, No. 2, pp. 187-198; Date of Publication: Apr. 1997.

Author: Takagi, N.; Kawata, Y.; Nikvi, N.; Morit, K.; Ohmatsu, H.; Kakinuma, R.; Eguchi, K.; Kusumoto, M.; Kaneko, M.; Moriyama, N.; Title: "Computerized characterization of contrast enhancement patterns for classifyting pulmonary nodules"; *Image Processing, 2000. Proceedings. 2000 International Conference* on vol. 1, pp. 188-191; Date of Publication: 2000.

Author: A. P. Reeves, W. J. Kostis; Title: "Computer-Aided Diagnosis of Small Pulmonary Nodules"; *Seminars in Ultrasound, CT. and MRI*, vol. 21, No. 2, pp. 116-128; Date of Publication: Apr. 2000.

Author: W. J. Kostis, A. P. Reeves, D. F. Yankelevitz, C.I. Henschke; Title: "Three-dimensional segmentation of solitary pulmonary nodules from helical CT scans"; *CARS '99 Computer Assisted Radiology and Surgery: Proceedings of the 13th International Congress and Exhibition*, pp. 203-207; Date of Publication: 1999.

Author: Li Fan, Carol L. Novak, Jiangzhong Qian, Gerhard Kohl, and David P. Naidich; Title: "Automatic Detection of Lung Nodules from Multi-Slice Low Dose CT Images"; Proc SPIE 2001; 4322:1828-1835; Date of Publication: 2001; Place of Publication: U.S.

Author: Binsheng Zhao, Anthony Reeves, David Yankelevitz, and Claudia Henschke; Title: "Three-Dimensional multi-criterion automatic segmentation of pulmonary nodules of helical CT images"; Optical Engineering, 38(8):1340-1347; Date of Publication: 1999.

Author: American Cancer Society; Title: "Cancer Facts & Figures 2002"; 1599 Clifton Road, NE, Atlanta, GA, 30329-4251.

Author: Claudia I. Henschke, D.P. Naidich, D.F. Yankelevitz, G. McGuinness, D.I. McCauley, J.P. Smith, D.M. Libby, M. W. Pasmantier, M. Vazquez, J. Koizumi, D. Flleder, N.K. Altorki, and O.S. Miettinen; Title: "Early Lung Cancer Action Project: Initial Findings on Repeat Screening"; Cancer Jul. 1, 2001; 92(1):153-159; Date of Publication: Jul. 1, 2001.

Author: S.G. Armato III, M.L. Giger, J.T. Blackburn, K. Doi, H. MacMahon; Title: "Three-dimensional approach to lung nodule detection in helical CT"; *SPIE*, vol. 3661, pp. 553-559; Date of Publication: 1999; Place of Publication: U.S.

Author: S.L. Lou, C.L. Chang, K.P. Lin and T. Chen; Title: "Object based deformation technique for 3-D CT lung nodule detection"; *SPIE*, vol. 3661, pp. 1544-1552; Date of Publication: 1999; Place of Publication: U.S.

Author: T. Okumura, T. Miwa, Jun-ichi Kako, S. Yamamoto, M. Matsumoto, Y. Tateno, T. Linua and T. Matsumoto; Title: "Image processing for computer-aided diagnosis of lung cancer screening system by CT (LSCT)"; *SPIE*, vol. 3338, pp. 1314-1322; Date of Publication: 1998; Place of Publication: U.S.

Author: M. Fiebich, C. Wietholt, B.C. Render, S.G. Armato, K.R. Hoffmann, D. Wormanns and S. Diederich; Title: "Automatic detection of pulmonary nodules in low-dose screening thoracic CT examinations"; *SPIE*, vol. 3661, pp. 1434-1439; Date of Publication: 1999; Place of Publication: U.S.

Author: H. Taguchi, Y. Kawata and N. Niki, H. Satoh, H. Ohmatsu, K. Eguchi, M. Kaneko and N. Moriyama; Title: "Lung cancer detection based on helical CT images using curved surface morphology analysis"; *SPIE*, vol. 3661, pp. 1307-1313; Date of Publication: 1999; Place of Publication: U.S.

Author: S-C B. Lo, S-L A. Lou, J-S Lin, M.T. Freedman, M.V. Chien and S.K. Mun; Title: "Artificial convolution neural Network techniques and applications for lung nodule detection"; *IEEE transactions on medical imaging*, vol. 14, No. 4, pp. 711-718; Date of Publication: 1995.

Author: W.J. Kostis; Title: "Three-dimensional computed tomographic image analysis for early cancer diagnosis in small pulmonary nodules"; Ph.D. dissertation, Cornell University; Date of Publication: 2001; Place of Publication: U.S.

Author: R. Kakinuma, H. Ohmatsu, M. Kaneko, K. Eguchi, K. Naruke, K. Nagai; Title: "Detection failures in spiral CT screening for lung cancer: analysis of CT findings"; Radiology, 212, pp. 61-66; Date of Publication: 1999.

Author: F. Li, S. Sone, H. Abe, H.M. MacMahon, S.G. Armato, K. Doi; Title: "Missed Lung Cancers in low-dose Helical CT Screening Obtained from a General Population"; scientific paper presentation, RSNA 87th scientific assembly and annual meeting, Nov. 25-30, 2001.

Author: M. Remy Jardin, F. Giraud, C-H Marquette; Title: "Pulmonary nodules: detection with thick section spiral CT versus conventional CT"; Radiology, 187(No. 2), pp. 513-520; Date of Publication: 1993.

Author: J.A. Buckley, W. W. Scott, S.S. Siegelman, et al.; Title: "Pulmonary nodules: effect of increased data sampling on detection with spiral CT and confidence in diagnosis"; Radiology, 196, pp. 395-400; Date of Publication: 1995.

Author: Y. Kawata, N. Niki, H. Ohmatsu, M. Kusumoto, R. Kakinuma, K. Mori, N. Nishiyama, K. Eguchi, M. Kaneko, and N. Moriyama; Title: "Tracking interval changes of pulmonary nodules using a sequence of three-dimensional thoracic images"; *In Medical Imaging 2000: Image Processing, Proceedings of SPIE*, vol. 3979, pp. 86-96; Date of Publication: 2000; Place of Publication: U.S.

Author: Y. Kawata, N. Niki, H. Ohmatsu, M. Kusumoto, R. Kakinuma, K. Mori, N. Nishiyama, K. Eguchi, M. Kaneko, and N. Moriyam; Title: "Analysis of evolving processes in pulmonary nodules using a sequence of three-dimensional thoracic images"; In M. Sonka d K.M. Hanson, editors, *Medical Imaging 2001: Image Processing, Proceedings of SPIE*, vol. 4322, pp. 1890-1901; Date of Publication: 2001; Place of Publication: U.S.

Author: Z.-H. Cho, J. P. Jones, and M. Singh. *Foundations of Medical Imaging*. John Wiley and Sons Inc.; Title: "X-Ray Computerized Tomography", pp. 148-164; Date of Publication: 1993; Place of Publication: U.S.

Author: A. K. Jain; Title: "Fundamentals of Digital Image Processing", Prentice Hall, Englewood Cliffs, NJ; pp. 384-389; Date of Publication: 1989; Place of Publication: U.S.

Author: S. N. Reske, R. Bares, U. Bull, A. Guhlmann. E. Moser, and M. F. Wannenmacher; Title: "[Clinical value of positron emission tomography (PET) in oncologic questions: results of an interdisciplinary consensus conference. Schirmerreschaft der Deutschen Gesellschaft for Nuklearmedizin.]" (Summary in English is provided on p. 42); *Nuklearmedizin*, 35(2):42-52; Date of Publication: Apr. 1996; Place of Publication: Germany.

Author: M. D. Seemann, T. Beinert, F. Spelsberg, B. Obst, H. Dienemann, U. Fink, P. Kohz, and M. Reiser; Title: "Differentiation of solitary pulmonary coin lesions by high-resolution computerized tomography" (Summary in English provided on p. 580); *Radiology*, 36(7):579-585; Date of Publication: Jul. 1996; Place of Publication: Germany.

Author: J. Serra; *Image analysis and mathematical morphology.*; pp. 34-92; Academic Press, London; Date of Publication: 1982; Place of Publication: London.

Author: J. Serra; Title: "Introduction to Morphological Filters"; *Image analysis and mathematical morphology; vol. 2: Theoretical advances*, pp. 101-114; Academic Press, London; Date of Publication: 1988; Place of Publication: London.

Author: S. W. Tamarkim; Title: "Spiral computed tomography and computed tomographic angiography"; In J. R. Haaga, C. F. Lanzieri, D. J. Sartoris, and E. A. Zehrouni, editors, *Computed tomography and magnetic resonance imaging of the whole body*, Mosby; pp. 1694-1706; Date of Publication: 1994; Place of Publication: U.S.

Author: W. Press; Title: "Numerical Recipes in C"; 2nd Edition, Cambridge University Press; pp. 402-420; Date of Publication: 1992; Place of Publication: unknown.

Author: M.S. Brown, M.F. McNitt-Gray, J.G. Goldin and D.R. Aberle; Title: "Model-based segmentation architecture for lung nodule detection in CT"; *RSNA 2000 annual meeting*.

Author: S.G. Erberich, K.S. Song, H. Arakawa, H.K. Huang, R. Webb, K.S. Hoo, B. W. Loo; Title: "Knowledge-based lung nodule detection from helical CT" (Text of Publication only as Figures are not available); *RSNA 1997 annual meeting*.

Author: K. Kanazawa, M. Kubo, N. Niki, H. Satoh, H. Ohmatsu, K. Eguchi, N. Moriyama; Title: "Computer Assisted Diagnosis of Lung Cancer Using Helical X-ray CT"; *Proceedings of ICPR*, pp. 381-385; Date of Publication: 1996; Place of Publication: U.S.

Author: N. Otsu; Title: "A threshold selection method from gray-level histograms"; IEEE Trans. Systems Man Cybernet, 9(1), pp. 62-66; Date of Publication: 1979; Place of Publication: Japan.

Author: C.L. Novak, D.P. Naidich, L. Fan, J. Qian, J.P. Ko, A.N. Rubinowitz; Title: "Improving Radiologists' Confidence of Interpreting Low-dose Multidetector Lung CT screening Studies Using an Interactive CAD system"; Scientific paper presentation. RSNA 87th scientific assembly and annual meeting, Nov. 25-30, 2001.

Author: S. G. Armato, III, F. Li, M.L. Giger; Title: "Performance of Automated CT Lung Nodule Detection on Missed Cancer"; scientific paper presentation, RSNA 87th scientific assembly and annual meeting, Nov. 25-30, 2001.

Author: M.K. Gurcan, N. Petrick, B. Sahiner, H.P. Chan, P.N. Cascade, E.A. Kazerooni, L.M. Hadjiiski; Title: "Computerized lung nodule detection on thoracic CT images: combined rule-based and statistical classifier for false positive reduction"; *SPIE*, vol. 4322, pp. 686-692; Date of Publication: 2001; Place of Publication: U.S.

Author: O. Karacan, O.A. Ibis, S. Akcay, O. Akkoca, F.O. Eyuboglu, and M. Coskun; Title: "Chest readiography and the solitary pulmonary nodule"; *Journal of Radiology*; Date of Publication: 2002; Place of Publication: unknown.

* cited by examiner

FIG. 3

| Structure | Mean | Low | High |
|---|---|---|---|
| Bone | 988 | 545 | 2570 |
| Parenchyma | 189 | 1 | 1125 |

FIG. 5

Lung Mask Generation Algorithm
1. Apply median and mean filters to the original scan to reduce noise.
2. Segment the scan into solid components and other structures via thresholding.
3. Identify and delete the surrounding background. (i.e. region that is not part of the thorax).
4. Label all connected components and select the lung region (the largest component).
5. Refine the geometric form of the resulting region by morphological filtering.

FIG. 7
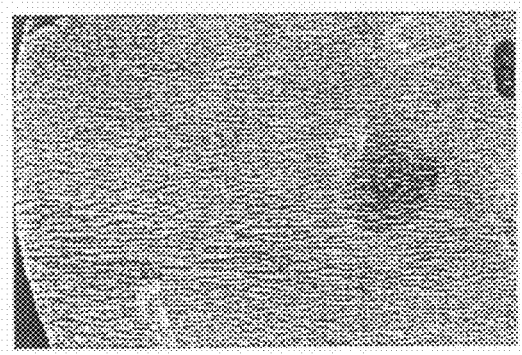
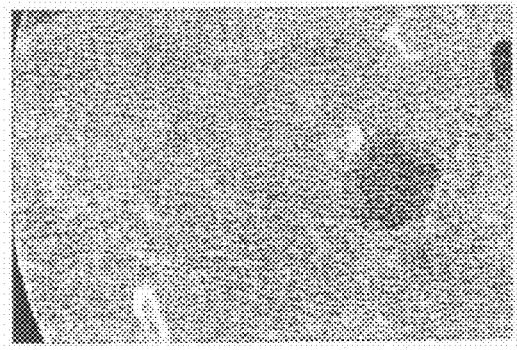
FIG. 8
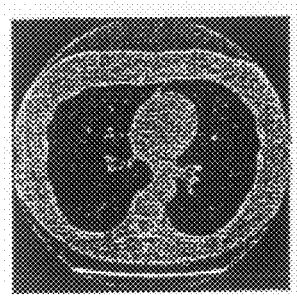
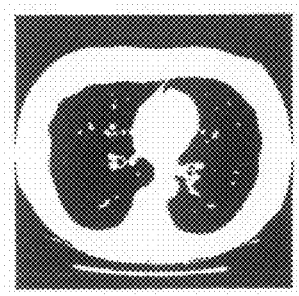
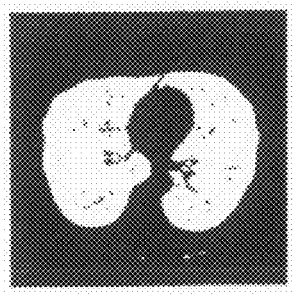

FIG. 13

|  | Morphological Filtering Running time |
|---|---|
| Fixed Kernel Size | 9 min, 10 sec |
| Variable Kernel Size | 5 min, 4 sec |

FIG. 15

Algorithm for finding the location $P'$ and size $r'$ of a nodule

1. Initial point $P_1 = (x_1, y_1, z_1)$ and size $r_1$.
2. Increase radius: $r_i = r_{i-1} + \Delta_r$
3. Compute best location: $P_i = \text{search}(P_{i-1}, r_i)$
4. Compute match (size metric): $\gamma_i = \text{size}(P_i, r_i)$
5. Repeat 2 through 4 until $\gamma_i < T$
6. $P' = P_i, r' = r_i$

FIG. 21

Detailed Algorithm for finding the location P and size r of a nodule

1. Given a high-resolution 3d CT image of a nodule.
2. Window the image to ignore any bone structures.
3. Define the locator and sizing template functions.
4. Define the initial location, $P$.
5. Define a termination criteria: *target*, $\epsilon$ and $\alpha$.
6. Set *rstart* = 1, *rstep* = 1, *rmax*, $\gamma = \infty$.
7. While ( | $\gamma$-*target* | > $\epsilon$) and (*rstep* > $\alpha$)
   (a) For $r_i$=*rstart* to *rmax* with increment of *rstep*
      i. Set the locator template radius to $r_i$.
      ii. Calculate the location: $P_i = search(P_{i-1}, r_i)$
      iii. Set the sizing template radius to $r_i$ and the location to $P_i$.
      iv. Calculate size: $\gamma$ = the response of the sizing template function.
      v. If ($\gamma$ < *target*), then exit the for loop (go to 7b).
   (b) Set *rstep* = *rstep* / $\alpha$
   (c) Set *rstart* = $r_{i-1}$ + *rstep*
   (d) Set $P_i = P_{i-1}$
8. Output the location and radius of the nodule, $P_i$, $r_i$.

FIG. 25

Hill-Climbing Search Algorithm for the nodule finding Algorithm

1. Given an initial condition, *initial* and a stepsize, *dt*.
2. *param = initial*
3. Evaluate the locator template function for movement of *dt* and -*dt* in the three directions from *param*.
4. If a smaller response is calculated, then move *param* in the appropriate direction for the largest decrease and goto 3.
5. Return the minimizing parameters, *param*.

FIG. 27

Algorithm for registering a first image, $im_1$, and a second image, $im_2$, using a rigid-body transformation

1. Convert both input images, $im_1$ and $im_2$, to floating point pixels.

2. If desired, mask either image by setting pixels to a background value.

3. Calculate the initial conditions for the rigid-body transformation on $im_1$.

4. Minimize (or maximize) the metric between $im_2$ and the rigid-body transformation of $im_1$ by changing the transformation parameters.

5. Using the best rigid-body transformation parameters, transform $im_1$, convert it back to the original pixel format, and output the image.

FIG. 28

Hill-Climbing Search Algorithm for determining the best rigid-body transformation parameters

1. Given an initial condition, *initial*, the translation stepsize, *dt*, the rotation stepsize, *dr*, and the number of passes, *p*
2. Inflate the stepsizes: $dt = dt * 2^{p-1}$, $dr = dr * 2^{p-1}$
3. *param = initial*
4. For *a* = 1 to p
    (a) Evaluate the metric for movement from *param* in the three translation directions with steps *dt* and -*dt* pixels.
    (b) Evaluate the metric for movement from *param* in the three rotation directions with steps *dr* and -*dr* degrees.
    (c) If a smaller metric value is calculated in (a) or (b), then move *param* in the appropriate direction for the largest decrease and goto (a).
    (d) Update stepsizes: $dt = dt/2$, $dr = dr/2$
5. Return the minimizing parameters, *param*.

FIG. 29

Algorithm for removing the pleural-surface given a location $P'$ near the center of the nodule.

1. Calculate the center of mass, $COM$, of the largest spherical volume centered at $P'$ that fits inside the image.
2. Determine the initial direction towards the pleural wall: $d' = \dfrac{COM - P'}{\|COM - P'\|}$
3. Initialize $P_0 = P'; d = d'$
4. Set $\gamma_{max} = 0.5; \gamma = 0; step = 1.5;$
5. While $\gamma < \gamma_{max}$ (a) Move location: $P_i = P_{i-1} + step * d$ (b) Calculate the plane $A$ normal to $d$ and passing through point $P_i$ (c) $mass_i$ = size of the cut nodule (the connected component region containing point $P_i$ and located on the negative side of plane $A_i$)

(d) Calculate the change in mass: $\Delta_i = mass_i - mass_{i-1}$ (e) Calculate the ratio change: $\gamma = \dfrac{\Delta_i}{\Delta_{i-1}} - 1$ (f) if $\gamma > \gamma_{max}$, then change $d$ to reorientate the plane $A_i$ to minimize the size of the cut nodule. Recalculate $mass_i$, $\Delta_i$, and $\gamma$.

6. Return the cut nodule using plane $A_{i-1}$.

FIG. 31

Algorithm for Recursively finding the cut nodule region, given the starting point $p = P'$, and the plane $A$, and the image $im$ 1. Mark the pixel $p$ as visited.
2. If point $p$ is not behind plane $A$ then exit.
3. Mark pixel located at $p$ as part of the region.
4. For each of the six possible one-pixel moves, calculate a new position $p'$. If the pixel $p'$ is foreground and has not been visited, then recursively call the algorithm using $p = p'$.

FIG. 32

Hill-Climbing Search Algorithm for removing the pleural surface

1. Given the initial direction, $d_0$ and a stepsize, $step_d$.
2. $d = d_0$
3. For each of the six possible $step_d$ steps from $d$, calculate the size of the cut-nodule.
4. If a smaller size is calculated, then move $d$ in the appropriate direction for the largest decrease, normalize $d$, and goto 3.
5. Return the minimizing direction $d$.

SYSTEM, METHOD AND APPARATUS FOR SMALL PULMONARY NODULE COMPUTER AIDED DIAGNOSIS FROM COMPUTED TOMOGRAPHY SCANS

CROSS-REFERENCE TO RELATED APPLICATIONS

This application is a divisional of U.S. patent application Ser. No. 10/245,782, filed Sep. 16, 2002 now abandoned, which claims the benefit of U.S. Provisional Application No. 60/322,038, filed Sep. 14, 2001, which are incorporated herein by reference.

BACKGROUND OF THE INVENTION

The present invention relates to the art of diagnostic imaging of small pulmonary nodules. In particular, the present invention is related to analyzing and manipulating computed tomography scans to: segment the lungs, measure lung volume, locate and determine the size of the nodules without explicit segmentation, register the nodules using a rigid-body transformation, and removing the pleural surface from juxtapleural nodules in thresholded images.

Lung cancer is the leading cause of cancer deaths among the population in the United States. Each year there are about 170,000 newly diagnosed cases of lung cancer and over 150,000 deaths. More people die of lung cancer than of colon, breast, and prostate cancers combined. Despite the research and improvements in medical treatments related to surgery, radiation therapy, and chemotherapy, currently the overall survival rate of all lung cancer patients is only about 14 percent. Unfortunately the survival rate has remained essentially the same over the past three decades. The high mortality rate of lung cancer is caused by the fact that more than 80% lung cancer is diagnosed after it has metastasized. Patients with early detection of lung cancer followed by proper treatment with surgery and/or combined with radiation and chemotherapy can improve their five-year survival rate from 13 percent to about 41 percent. Given that earlier-stage intervention leads to substantially higher rates of survival, it is therefore a major public health directive to reduce the mortality of lung cancer through detection and intervention of the cancer at earlier and more curable stages.

The development of the computed tomography (CT) technology and post-processing algorithms has provided radiologists with a useful tool for diagnosing lung cancers at early stages. However, current CT systems have their inherent shortcomings in that the amount of chest CT images (data) that is generated from a single CT examination, which can range from 30 to over 300 slices depending on image resolution along the scan axial direction, becomes a huge hurdle for the radiologists to interpret. Accordingly, there is a constant need for the improvement and development of diagnostic tools for enabling a radiologist to review and interpret the vast amount of information that is obtained through a CT examination.

International Publication No. WO 01/78005 A2 discloses a system and method for three dimensional image rendering and analysis, and is incorporated herein by reference. The system performs a variety of tasks that aid a radiologist in interpreting the results of a CT examination.

One task that radiologists focus on is segmenting the lung region from the image of a single slice obtained from the CT examination. In the prior art, some have suggested using a linear discriminant function and morphological filtering to automatically segment the lungs (S. Hu, E. A. Hoffman, and J. M. Reinhardt, "Automatic Lung Segmentation for Accurate Quantitation of Volumetric X-Ray CT Images," *IEEE Transactions on Medical Imaging*, Vol 20, No 6, June 2001, which is incorporated herein by reference) while others have used mean and median filtering to remove the streaking artifacts due to excessive x-ray quantum noise (J. Hsieh, "Generalized Adaptive Median Filters and their Application in CT," *SPIE*, Vol 2299, 1994; J. Hsieh, "Adaptive Trimmed Mean Filter for CT Imaging," *SPIE*, Vol 2299, 1994 which is incorporated herein by reference).

Radiologists also study the location and size of the pulmonary nodules in the CT scan. It is preferred if the radiologist could perform this analysis without the use of explicit segmentation. In some prior work, the location of a nodule was determined by finding the center of mass of the nodule through an iterative correlation-based procedure (A. P. Reeves, W. J. Kostis, D. F. Yankelevitz, C. I. Henschke, "Analysis of Small Pulmonary Nodules without Explicit Segmentation of CT images," *Radiological Society of North America*—2000 *Scientific Program*, vol. 217, pgs. 243-4, November 2000 which is incorporated herein by reference). The method works for isolated pulmonary nodules, but fails on nodules attached to the pleural surface.

Radiologists also estimate a measurement of doubling time of a nodule by registering two separate images of the nodule taken at two different times (time-1 and time-2). This analysis requires that the time-1 and time-2 nodules be registered correctly so that the growth can be properly measured. Other objects such as vessels and bronchial tubes must also be registered together. This results in their absence in the difference image and little effect on the growth measurement. Previously, two nodules were registered by finding the centers of mass of the nodules and translating the image accordingly (A. P. Reeves, W. J. Kostis, D. F. Yankelevitz, C. I. Henschke, "Analysis of Small Pulmonary Nodules without Explicit Segmentation of CT images," *Radiological Society of North America*—2000 *Scientific Program*, vol. 217, pgs. 243-4, November 2000 which is incorporated herein by reference). However, this analysis did not guarantee that the two nodules would be correctly orientated, and that the other objects in the image would registered because these objects might be rotated about the nodule. Some have registered the nodules by performing a maximization search of the mutual information metric over the rigid-body transformation parameters (F. Maes, A. Collignon, D. Vandermeulen, G. Marchal and P. Suetens, "Multimodality image registration by maximization of mutual information," *IEEE Transactions on Medical Imaging*, vol. 16, no. 2, pgs. 187-198, April 1997; Takagi, N.; Kawata, Y.; Nikvi, N.; Morit, K; Ohmatsu, H.; Kakinuma, R.; Eguchi, K.; Kusumoto, M.; Kaneko, M.; Moriyama, N. "Computerized characterization of contrast enhancement patterns for classifying pulmonary nodules" *Image Processing, 2000. Proceedings. 2000 International Conference on*, vol. 1, pgs. 188-191, 2000 which are incorporated herein by reference).

Radiologists also need to remove the pleural surface from juxtapleural nodules in CT images. In some prior work, three-dimensional morphological filtering and mathematical moments were used to segment a juxtapleural nodule from pleural surface in a binary image (A. P. Reeves, W. J. Kostis, "Computer-Aided Diagnosis of Small Pulmonary Nodules,"

Seminars in Ultrasound, CT, and MRI, vol. 21, no. 2, pgs. 116-128, April 2000 which is incorporated herein by reference).

SUMMARY OF THE INVENTION

The present invention is directed to diagnostic imaging of small pulmonary nodules. There are two main stages in the evaluation of pulmonary nodules from Computed Tomography (CT) scans: detection, in which the locations of possible nodules are identified, and characterization, in which a nodule is represented by measured features that may be used to evaluate the probability that the nodule is cancer. Currently, the most useful prediction feature is growth rate, which requires the comparison of size estimates from two CT scans recorded at different times. The present invention includes methods for detection and feature extraction for size characterization. The invention focuses the analysis of small pulmonary nodules that are less than 1 centimeter in size, but is also suitable for larger nodules as well.

For the purpose of Computer Aided Diagnosis (CAD), pulmonary nodules are dichotomized into attached nodules and isolated nodules based on their location with respect to other solid lung structures. Attached nodules are adjacent to some larger solid structure, such as the pleural surface. Isolated nodules consist of both well-circumscribed nodules and nodules that are larger than all adjacent structures, such as blood vessels or bronchi. Nodules themselves may be solid, non-solid or part-solid. The analysis of a CT scan for the existence and study of pulmonary nodules generally entails the following:

1. Detection (a) Identify the lung regions and main bronchi from thoracic CT images (b) Separate the lungs into two major regions: (1) the lung parenchyma and (2) the lung surface region, including the pleural surface and major airways.

(c) Identify possible locations of isolated nodules in the lung parenchyma region and identify possible locations of attached nodules in the in the lung surface regions.

2. Characterization (a) Starting with a single location point within a possible nodule, identify the nodule region in the CT images. This entails locating the geometric center of the nodule and approximating its size.

(b) Given the location and approximate size of a nodule, compute characteristic features of the nodule, including robust size estimates.

In connection with the overall methodology of analyzing CT scans, the present invention includes sub-methods for the following:

1. The segmentation of whole lung CT scans into lung parenchyma and lung surface regions The first preprocessing stage in CT lung image analysis is to obtain the regions of interest from the whole lung scans. The lung region consists of all tissue found within the pleural surface, including lung parenchyma, vessels, and possibly nodules. Features of this approach are the partitioning of the lung into three major regions and the tailoring of the segmentation algorithm for each region. In addition a distinction is made between the central lung parenchyma and the region of the of the lung parenchyma near to the lung walls. A properly segmented lung region greatly reduces the search space of an entire CT scan.

2. The characterization of lung air volume and inspiration both from the entire parenchyma region and from single axial CT images The total volume of the lungs is estimated from the whole lung scans. In addition the change in volume between different scans due to changes in inspiration is also addressed.

3. The automatic location and size characterization of nodules

An algorithm finds the center and approximate size of pulmonary nodules in CT images without the use of explicit segmentation. The algorithm has a weighting function that locates the center of mass of the nodule. A second weighting function, centered on the location of the first weighting function, estimates the size of the nodule. The process is repeated with weighting functions of increasing size until the size of the nodule region is reliably determined. The algorithm works for both isolated nodules and nodules attached to the walls.

The algorithm is designed for use on images that are resampled from high-resolution CT scans (1 mm slice thickness) into an isotropic voxel space. Such a system could be useful in helping radiologists analyze pulmonary nodules. In the CT image browser, the radiologist could click on a nodule and, using the algorithm, the computer could automatically locate the center and size of the nodule. Using this information, the computer then clips out a region of interest for the nodule and performs some nodule characterization analysis and perhaps some 3D visualization.

4. The registration of nodules from two scans

An algorithm registers two different scans of a nodule region. A three-dimensional rigid-body transformation of one scan is made to optimally match the location and orientation (6-degrees of freedom) of the second scan. Powell's method is the preferred search strategy.

The analysis of pulmonary nodules without explicit segmentation estimates a measurement of doubling time by applying a weighted function on the difference image of the two nodules. The analysis requires that the time-1 and time-2 nodules be registered correctly so that the growth can be properly measured. Other objects such as vessels and bronchial tubes must also be registered together, resulting in their absence in the difference image and little effect on the growth measurement.

5. The segmentation of nodules attached to the pleural surface.

An algorithm segments nodules that are attached to the pleural surface from the pleural surface. Starting from a location within a nodule, the direction of the pleural surface is determined. A cutting plane is then iteratively moved towards the surface until the volume of the region behind the wall suddenly increases. The increase in volume indicates that the pleural surface has been reached. The orientation and location of the plane is then preferably optimized by a hill climbing procedure.

The algorithm removes the pleural surface (and any other extraneous objects) from a high-resolution image containing a juxtapleural nodule. The algorithm is not only required to perform a good segmentation, but expected to perform the same segmentation when given different scans of the same nodule. This property is necessary because the resulting segmented nodule will be used for the characterization and analysis of the nodule. If the segmentation is not performed consistently between images scanned at different times, then the doubling time estimation will not be accurate.

A preferred embodiment of the present invention is a method and apparatus for generating a lung mask for segmenting a lung image from voxel data containing the lung image, noise, solid components and surrounding background information. The apparatus of the invention is a masking unit configured with the teachings of the method of the invention. The invention can also be practiced on a machine readable medium. The method includes initially applying a median filter and a mean filter to the voxel data to reduce noise. The noise reduced voxel data is then thresholded to identify solid components and other structures. The surrounding background in the noise reduced voxel data is identified and deleted. The connected components of the voxel data are labeled, and the largest connected components are determined to select a lung region having a geometric form. The voxel data is morphological filtered to refine the geometric form of the lung region.

In a preferred embodiment, the voxel data is associated with a plurality of slices through a patient's lung with the slices beginning at about the patient's shoulders and the application of the median filter and the mean filter is performed for the first 25 percent of the plurality of slices only to substantially reduce the computation time. Preferably the median filter has a size of 4×4, and the mean filter has a size of 1×3. Preferably the voxel data in step is thresholded at a gray level of about 500. Preferably the largest connected components are selected to be associated with more than about 1 percent of the voxel data. Preferably the voxel data is associated with a plurality of slices for the morphological filtering with the slices being divided into a first end region, a middle region, and a second end region. The morphological filtering is preferably performed with 2D circular filter having a first diameter in the first end region and the second end region while being performed with 2D circular filter having a second diameter which is about twice the first diameter in the middle region.

The present invention also includes a method and apparatus for measuring lung volume from a segmented lung image. The lung image is obtained from a scan which includes a plurality of slices of voxel data having a gray level value and a volume associated therewith. The apparatus of the invention is a lung volume measuring unit configured with the teachings of the method of the invention. The invention can also be practiced on a machine readable medium. The method includes initially generating a matrix of entries from the segmented lung image. The matrix includes a plurality of columns and a plurality of rows. Each of the plurality of columns represent the gray level value and each of the plurality of rows represent one of the plurality of slices in the scan with the entries corresponding to the number of times that the gray level occurs in the corresponding slice. The number of voxels in the segmented lung image is next determined from the matrix entries. The number of voxels in the segmented lung image is multiplied by the volume of each voxel.

The present invention also includes a method and apparatus for measuring volume of tissue in a segmented lung image. The lung image is obtained from a scan which includes a plurality of slices of voxel data having a gray level value and a volume associated therewith. The apparatus of the invention is a lung tissue measuring unit configured with the teachings of the method of the invention. The invention can also be practiced on a machine readable medium. The method includes initially generating a matrix of entries from the segmented lung image. The matrix includes a plurality of columns and a plurality of rows. Each of the plurality of columns represent the gray level value and each of the plurality of rows represent one of the plurality of slices in the scan with the entries corresponding to the number of times that the gray level occurs in the corresponding slice. The sum of tissue of voxels in the segmented lung image is next determined from the matrix entries. The sum of tissue of voxels in the segmented lung image is multiplied by the volume of each voxel. The sum of tissue of voxels is preferably calculated by summing the product of each matrix entry multiplied by the corresponding gray level value divided by a gray level value assigned for tissue.

The present invention also includes a method and apparatus for finding the location, P', and size, r', of a pulmonary nodule in a high-resolution computed tomography (CT) image. The apparatus of the invention is a nodule finding unit configured with the teachings of the method of the invention. The invention can also be practiced on a machine readable medium. In the method, a set of initial processing parameters including an initial location, $P_1$, an initial size, $r_1$, and target value, T, is initially selected. An initial new location $P'_i$ of the nodule is computed with a locator template function. After incrementally increasing size, $r_i$, a new location $P'_i$ of the nodule is computed with the locator template function, and a size metric is computed with a sizing template function. The size, $r_i$, is incrementally increased while determining a new location $P'_i$ of the nodule and computing the size metric until the size metric is less than the target value. The location, P', and the size, r', is then returned from the previous iteration of increasing size, $r_i$.

A preferred method for finding the location, P, and size, r, of a pulmonary nodule in a high-resolution computed tomography image initially includes windowing the image to ignore bone structures, and selecting a locator template function and a sizing template function. A set of initial processing parameters including: an initial location, P; size, r, and termination criteria is selected. A search is performed to determine a maximum response of the locator template function. A response of the sizing template function is determined and compared to the termination criteria. If the termination criteria has not been satisfied, the size, r, is incrementally increased, the response functions are determined and compared to the termination criteria. Once the termination criteria are satisfied the location, P, and size, r, of the nodule are outputted.

In the preferred method for finding the location, P, and size, r, of a pulmonary nodule in a high-resolution computed tomography image, preferably the image at intensities over about 1000 are clipped to window the image. Preferably the locator template function is either, a Gaussian template function, a Laplacian of the Gaussian template function, or a difference of Gaussians template function. The template function preferably has at least four parameters corresponding to the x-location, y-location, z-location, and radius. The initial location, P, can generally be either calculated from the image or specified by a user. Preferred methods for searching include a hill climbing method and Powell's method.

The present invention also includes a method and apparatus for registering 3-d images of a pulmonary nodule from a high-resolution computed tomography (CT) scans. The images include a first image ($im_1$) obtained at time-1 and a second image ($im_2$) obtained at time-2, and are in a floating point pixel-format associated with a 6-dimensional parameter space. The apparatus of the invention is a registering unit configured with the teachings of the method of the invention. The invention can also be practiced on a machine readable medium. The method includes calculating initial rigid-body transformation parameters for a rigid-body transformation on the first image ($im_1$). The optimum rigid-body transformation parameters are determined by calculating a registration metric between the second image ($im_2$) and the rigid-body transformation on the first image ($im_1$). A registered image is generated from the optimum rigid-body transformation parameters.

In a preferred method for registering 3-d images of a pulmonary nodule from a high-resolution computed tomography (CT) scans, the calculation of the initial rigid-body transformation parameters is preferably preceded by masking one of the images by setting pixels to a background value. Preferably the background value is about −1000. The registration metric is generally either minimized or maximized. In one preferred embodiment, the registration metric is preferably calculated by:

transforming the first image ($im_1$) with the initial rigid-body transformation parameters to obtain a transformed first image ($im_{1t}$);

calculating the registration metric as a correlation (C.) between the transformed first image ($im_{1t}$) and the second image ($im_2$); and searching for the maximum correlation (C.) in the 6-dimensional parameter space.

In another preferred embodiment, the registration metric is preferably calculated by:

transforming the first image ($im_1$) with the initial rigid-body transformation parameters to obtain a transformed first image ($im_{1t}$);

calculating the registration metric as a mean-squared-difference (MSD) between the transformed first image ($im_{1t}$) and the second image ($im_2$); and searching for the minimum mean-squared-difference (MSD) in the 6-dimensional parameter space.

The transforming of the first image ($im_1$) to obtain the transformed first image ($im_{1t}$) is preferably a mapping of a point v in 3-d space to a point v' in transformed space defined by:

$$v' = R_x R_y R_z v + \begin{bmatrix} t_x \\ t_y \\ t_z \end{bmatrix}$$

wherein $R_x$, $R_y$, and $R_z$ are rotation matrices defined as:

$$R_x = \begin{bmatrix} 1 & 0 & 0 \\ 0 & \cos(r_x) & -\sin(r_x) \\ 0 & \sin(r_x) & \cos(r_x) \end{bmatrix}$$

$$R_y = \begin{bmatrix} \cos(r_y) & 0 & \sin(r_y) \\ 0 & 1 & 0 \\ -\sin(r_y) & 0 & \cos(r_y) \end{bmatrix}$$

$$R_z = \begin{bmatrix} \cos(r_z) & -\sin(r_z) & 0 \\ \sin(r_z) & \cos(r_z) & 0 \\ 0 & 0 & 1 \end{bmatrix}.$$

The initial rigid-body transformation parameters preferably include six parameters (tx,ty,tz,rx,ry,rz) respectively defined as translation in x, translation in y, translation in z, rotation about the x-axis, rotation about the y-axis, and rotation about the z-axis. Preferably the initial rotation parameters (rx,ry,rz) are all set to zero, and the initial translation parameters (tx, ty,tz,) are set so that the nodule in the first image ($im_1$) overlaps the nodule in the second image ($im_2$) during the initial calculation of the registration metric. The initial translation parameters (tx,ty,tz,) can be set to a difference between the center of the first image ($im_1$) and the center of the second image ($im_2$). Preferably the initial translation parameters (tx, ty,tz) are set to a difference between the center of mass of the first image ($im_1$) and the center of mass of the second image ($im_2$). The searching is can be conducted by calculating the correlation (C) or mean-squared-difference (MSD) for every possible set of rigid-body transformation parameters. Preferably the searching is conducted by either a Hill-Climbing search method or by Powell's method.

The present invention also includes a method and apparatus for removing extraneous matter from an image having a juxtapleural nodule. The apparatus of the invention is a processing unit configured with the teachings of the method of the invention. The invention can also be practiced on a machine readable medium. The method includes providing an initial location P'. A spherical volume that fits inside the image and is centered at the initial location P' is calculated. A center of mass, COM, of the spherical volume is calculated. An initial direction d' directed towards the extraneous matter is determined in accordance with the following equation:

$$d' = \frac{COM - P'}{\|COM - P'\|}.$$

A current location $P_i$ is initialized to be equal to the initial location P'. A current direction $d_i$ is initialized to be equal to the initial direction d'. A maximum ratio $\gamma_{max}$, step size s, prior mass $mass_{i-1}$, and prior change in mass $\Delta_{i-1}$ are initialized. The current location $P_i$ is moved by the step size s in the current direction $d_i$. An equation defining a plane A is determined so that the plane A is normal to the current direction $d_i$ and the plane A passes through the current location $P_i$. A current mass, $mass_i$, is calculated of the nodule on a side of the plane A opposing that of the extraneous matter. A current change in mass $\Delta_i$ is calculated by subtracting the prior mass $mass_{i-1}$ from the current mass mass. A current ratio $\gamma$ is calculated in accordance with the following equation:

$$\gamma = \frac{\Delta_i}{\Delta_{i-1}} - 1.$$

The prior mass $mass_{i-1}$ is set equal to the current mass mass. The prior change in mass $\Delta_{i-1}$ is set equal to the current change in mass $\Delta_i$. The current ratio $\gamma$ is compared to the maximum ratio $\gamma_{max}$. The current direction $d_i$ is modified to minimize the current mass $mass_i$, and the above steps are repeated starting with moving the current location $P_i$ by the step size s in the current direction $d_i$ while the current ratio $\gamma$ is one of less than and equal to the maximum ratio $\gamma_{max}$. The area of the nodule partitioned by the plane A is output in response to the current ratio $\gamma$ being greater than the maximum ratio $\gamma_{max}$.

In the preferred method for removing extraneous matter from an image having a juxtapleural nodule, the extraneous matter can include a pleural surface. Preferably the maximum ratio $\gamma_{max}$ is initialized to 0.5 and initializing the step size s is initialized to 1.5. Preferably the method also includes following the steps after the current ratio $\gamma$ is determined to be greater than the maximum ratio $\gamma_{max}$:

defining the current location $P_i$ as being visited;

determining on which side of the plane A the current location $P_i$ is located;

terminating in response to the current location $P_i$ not being located on a side of the plane opposing that of the extraneous matter;

defining the current location $P_i$ as being part of a region of interest in response to the current location $P_i$ being located on the side of the plane opposing that of the extraneous matter; and performing these additional steps recursively using a location corresponding to at least one of six (6) one-pixel moves from the current location $P_i$.

Preferably the step where the current direction $d_i$ is modified to minimize the current mass $mass_i$ and the step where the area of the nodule partitioned by the plane A is output in response to the current ratio $\gamma$ being greater than the maximum ratio $\gamma_{max}$ include the steps of:

calculating recursively the current mass $mass_i$ of the nodule on a side of the plane A opposing that of the extraneous matter using at least one of six (6) directions and a step size $s_1$ from the current location $P_i$; and defining the current direction $d_i$ equal to the direction yielding the largest decrease in the current mass $mass_i$.

Preferably the initial location P' is located near a center of the nodule.

For a better understanding of the present invention, reference is made to the following description to be taken in conjunction with the accompanying drawings and its scope will be pointed out in the appended claims.

BRIEF DESCRIPTION OF THE DRAWINGS

Preferred embodiments of the invention have been chosen for purposes of illustration and description and are shown in the accompanying drawings, wherein:

FIG. 3 is a table illustrating the densities of structures within the lungs;

FIG. 5 is a lung mask generation algorithm;

FIG. 7 illustrates on the left hand side the horizontal streaking artifacts due to beam hardening that can be reduced as shown on the right hand side with median and mean filtering;

FIG. 8 illustrates an original computer tomography scan on the left hand side with the image shown after thresholding in the center and the resulting image after the background has been identified, removed and inverted shown on the right hand side;

FIG. 13 illustrates a table illustrating the timed execution of morphological filtering using both fixed (28 pixel diameter) and varying (28 pixel and 14 pixel diameter) structuring elements;

FIG. 15 illustrates an algorithm for finding the location and size of a nodule;

FIG. 21 illustrates a detailed algorithm for finding the location and size of a nodule;

FIG. 25 illustrates a hill climbing search algorithm for the nodule finding algorithm;

FIG. 27 illustrates an algorithm for registering a first image and a second image using a rigid-body transformation;

FIG. 28 illustrates a hill climbing search algorithm for determining the best rigid-body transformation parameters for the registering algorithm;

FIG. 29 illustrates an algorithm for removing the pleural surface from juxtapleural nodules;

FIG. 31 illustrates an algorithm for recursively finding the cut nodule region; and FIG. 32 illustrates a hill climbing search algorithm for the algorithm for removing the pleural surface.

DETAILED DESCRIPTION OF THE INVENTION

Figure 1:
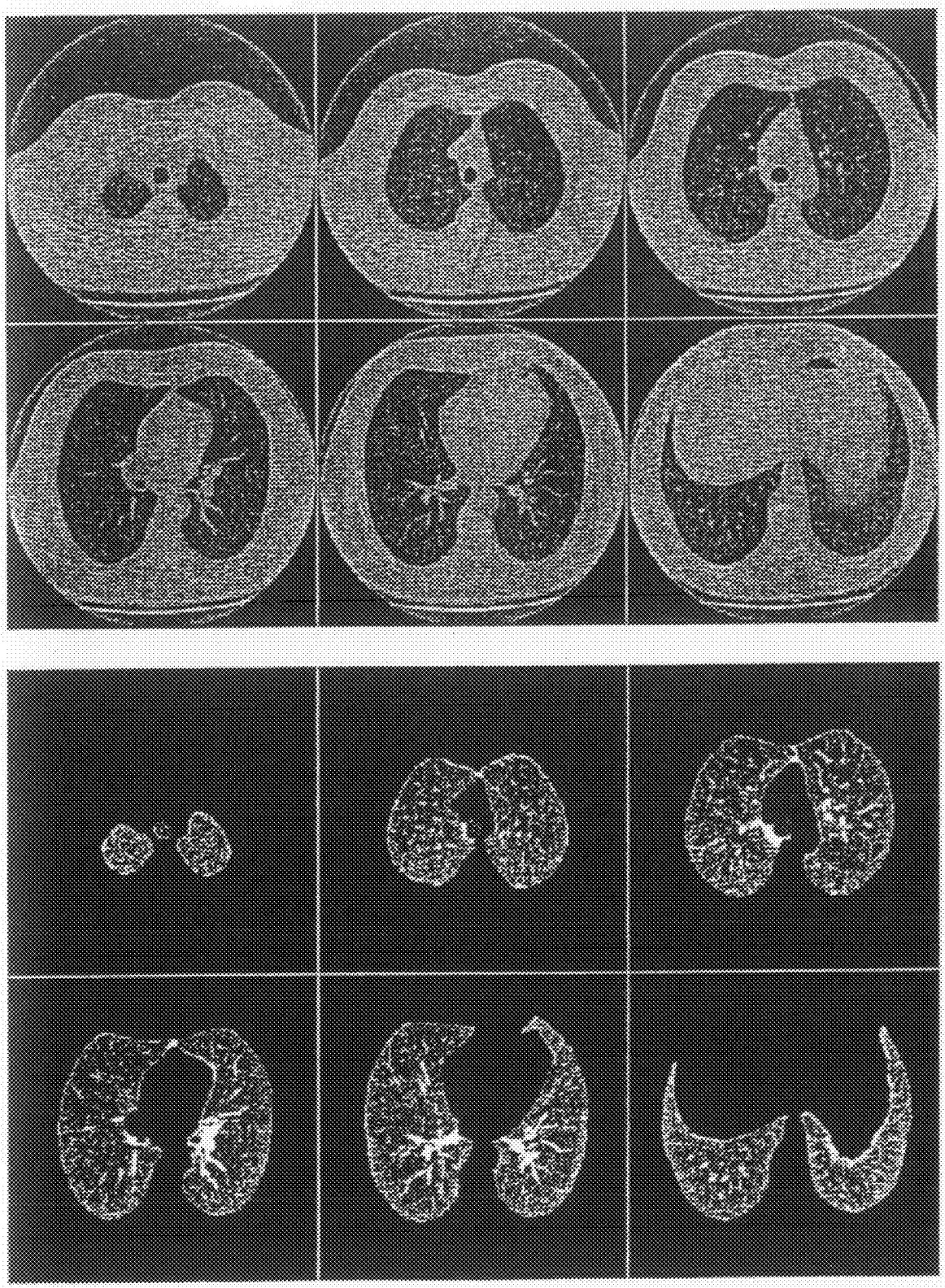
FIG. 1 illustrates at the top six (6) images that are selected slices from a single computer tomography scan along with the corresponding extracted lung regions from the selected slices at the bottom.

A system in accordance with the present invention may include a scanner, processor, memory, display device, input devices, such as a mouse and keyboard, and a bus connecting the various components together. The system may be coupled to a communication medium, such as a modem connected to a phone line, wireless network, or the Internet.

The present invention is preferably implemented using a general purpose digital computer, microprocessor, microcontroller, or digital signal processor programmed in accordance with the teachings of the present specification, as will be apparent to those skilled in the computer art. Appropriate software coding may be readily be prepared by skilled programmers based on the teachings of the present disclosure, as will be apparent to those skilled in the software art.

The present invention preferably includes a computer program product, which includes a storage medium comprising instructions that can be used to direct a computer to perform processes in accordance with the invention. The storage medium preferably includes, but is not limited to, any type of disk including floppy disks, optical data carriers, compact discs (CD), digital video discs (DVD), magneto-optical disks, read only memory (ROM), random access memory (RAM), electrically programmable read only memory (EPROM), electrically erasable programmable read only memory (EEPROM), magnetic or optical cards, or any type of media suitable for storing information.

Stored on any one of the above described storage media, the present invention preferably includes programming for controlling both the hardware of the computer and enabling the computer to interact with a human user. Such programming may include, but is not limited to, software for implementation of device drivers, operating systems, and user applications. Such storage media preferably further includes programming or software instructions to direct the general purpose computer to perform tasks in accordance with the present invention.

The programming of the computer preferably includes software for digitizing and storing images obtained from the image acquisition device (helical computed tomography scanner). Alternatively, it should be understood that the present invention may also be implemented to process digital data derived from images obtained by other means, such as x-rays and magnetic resonance imaging (MRI), positron emission tomography (PET), ultrasound, optical tomography, and electrical impedance tomography.

The invention may also be implemented by the preparation of application specific integrated circuits (ASIC), field programmable gate arrays (FPGA), or by interconnecting the appropriate component devices, circuits, or modules, as will be apparent to those skilled in the art.

A. Lung Segmentation

This section discusses a lung segmentation algorithm in detail. First the model of the lungs will be presented with a discussion of the difficulties with this task. Then each stage of the algorithm is presented.

Referring now to FIG. 1, the object of the algorithm is illustrated. The top 6 images in FIG. 1 are selected slices from a single CT scan, and the bottom 6 images are the lung regions extracted from those slices. The lungs are modeled as a low density region surrounded by a high density one. Image filtering is preferably first performed to minimize the effects of image noise. A simple linear discriminant function based on CT voxel values (photon density) is preferably used to partition the scan into lung parenchyma and solid structures. Further filtering can be used to compensate for imperfections in the thresholding.

Figure 2:
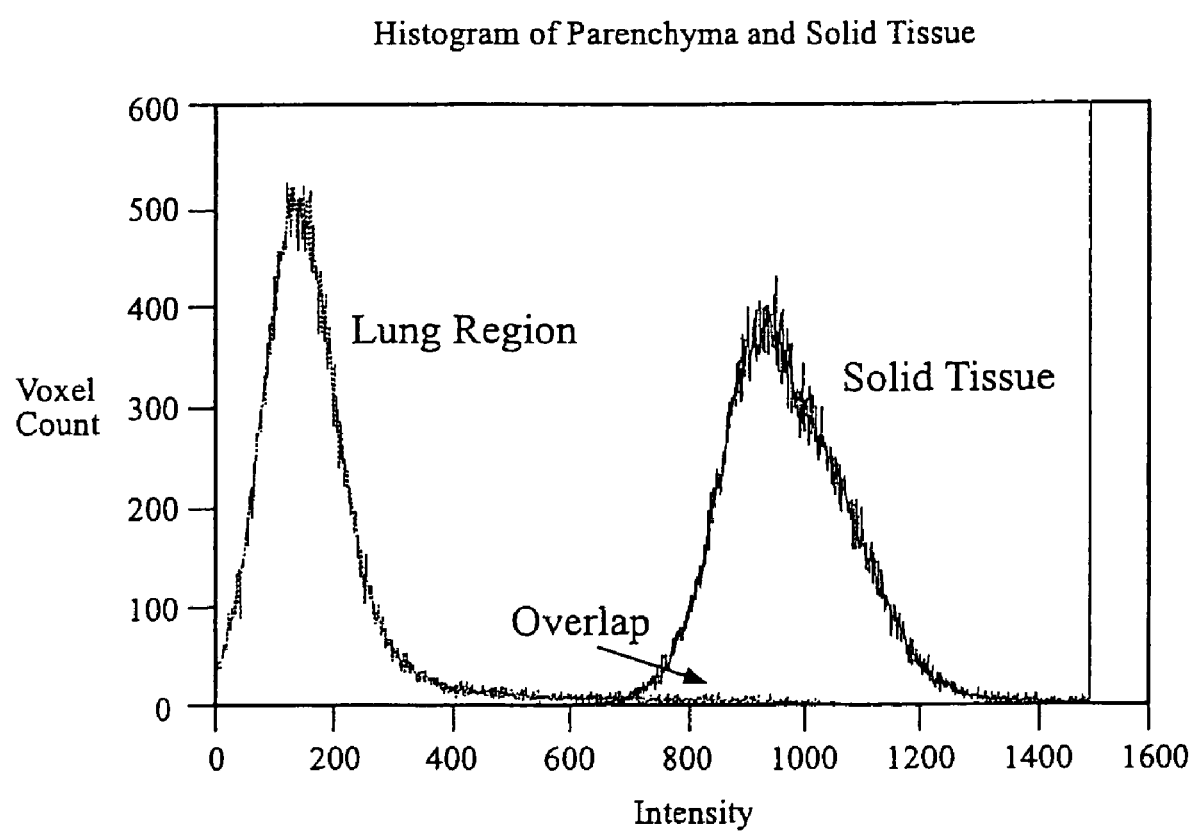
FIG. 2 illustrates a histogram of image intensity of the lung region that includes parenchyma, vessels, and nodules and other solid structures such as bone and organs.

The photon density of the structures within the lungs may be found by manually segmenting the lung into different regions and analyzing the results. Referring to FIG. 3, a table presents the range and mean values for the intensity of solid tissue and lung parenchyma. These values were obtained by manually selecting regions within a lung CT scan. Regions of at least 100,000 voxels were selected from four 2.5 mm full lung scans. The distribution of intensities is shown in FIG. 2. Note that there is an overlap between the intensity of the lung region and the intensity of the surrounding solid tissue.

Referring again to the table in FIG. 3, it is almost possible to partition lung parenchyma and bone using a linear discriminant function. All voxels with a gray level value less than 500 can be considered parenchyma because the minimum intensity for solid tissue is 545. Unfortunately, vessels, nodules, and partial voxels can not be partitioned so distinctly. Using the linear discriminant function as described will result in classification errors where the histograms in FIG. 2 overlap, most prominently between gray levels of 550 to 800. All values of gray level and intensity in the application are in GE units which equates to Hounsfield units HU as follows: HU=GE units−1024, for example 1000 GE=−24 HU.

One major challenge is handling the streaking artifacts found in 2.5 mm scans with a low radiation dose and a high pitch, such as those done in screening studies. When an X-ray beam passes through a region with a high attenuation coefficient, the remaining beam contains a greater proportion of high energy. This makes the path-integral of attenuation a non-linear function of distance (J. Hsieh, "Adaptive Trimmed Mean Filter for CT Imaging," *SPIE*, Vol 2299, 1994; H. Soltanian-Zadeh, J. P Windham and J. Soltanianzadeh, "CT Artifact Correction: An Image Processing Approach," *SPIE*, Vol 2710, 1996 which is incorporated herein by reference). In the case of lung CT scans, this artifact is prevalent through the shoulders, resulting in noise in the first 25% of the slices. The noise is characterized as both high intensity and low intensity horizontal streaks running through the image.

Figure 4:
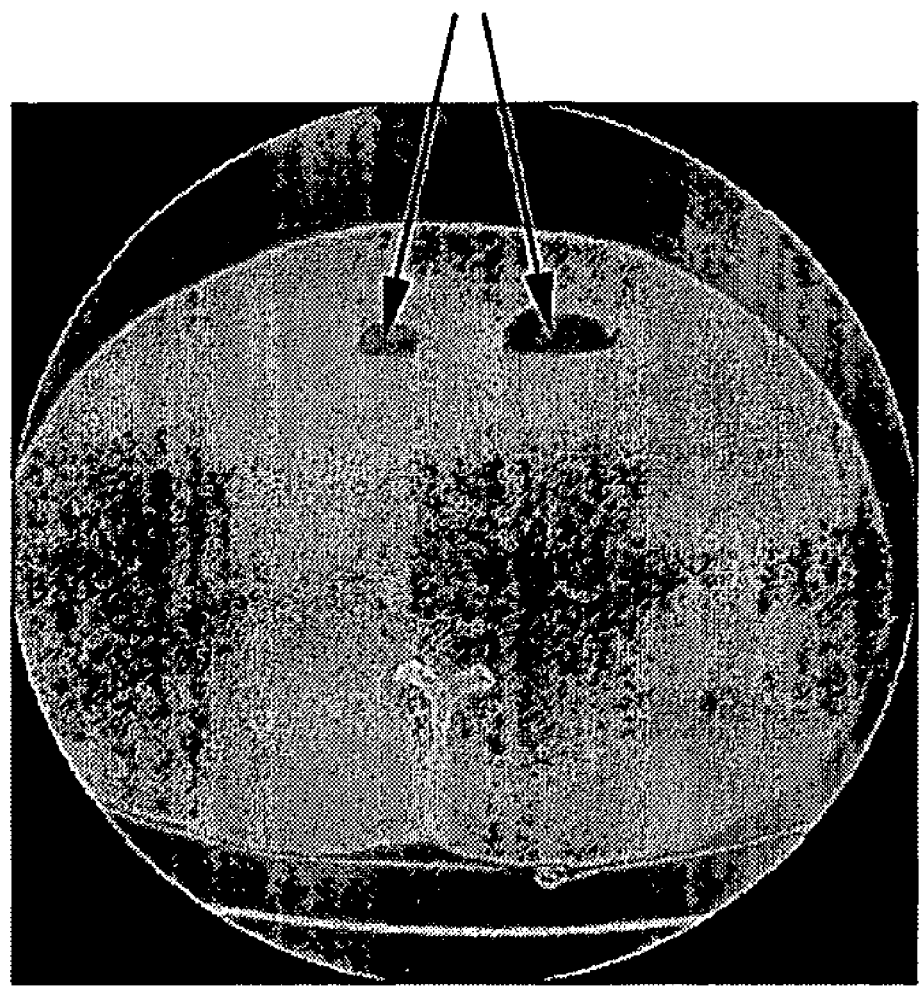
FIG. 4 illustrates an air pocket that is not part of the lungs but has similar characteristics to the modeling of the lungs.

Finally, there are other structures which confound the segmentation scheme. Air or gas found outside of the lungs will have the same characteristics as the lung themselves. Specifically they consist of a low density region surrounded by a high density one. It is necessary to discriminate between the lungs and other stray tissue or air pockets. An example of such a region is shown in FIG. 4, which occurs well below the lungs and the diaphragm.

Figure 6:
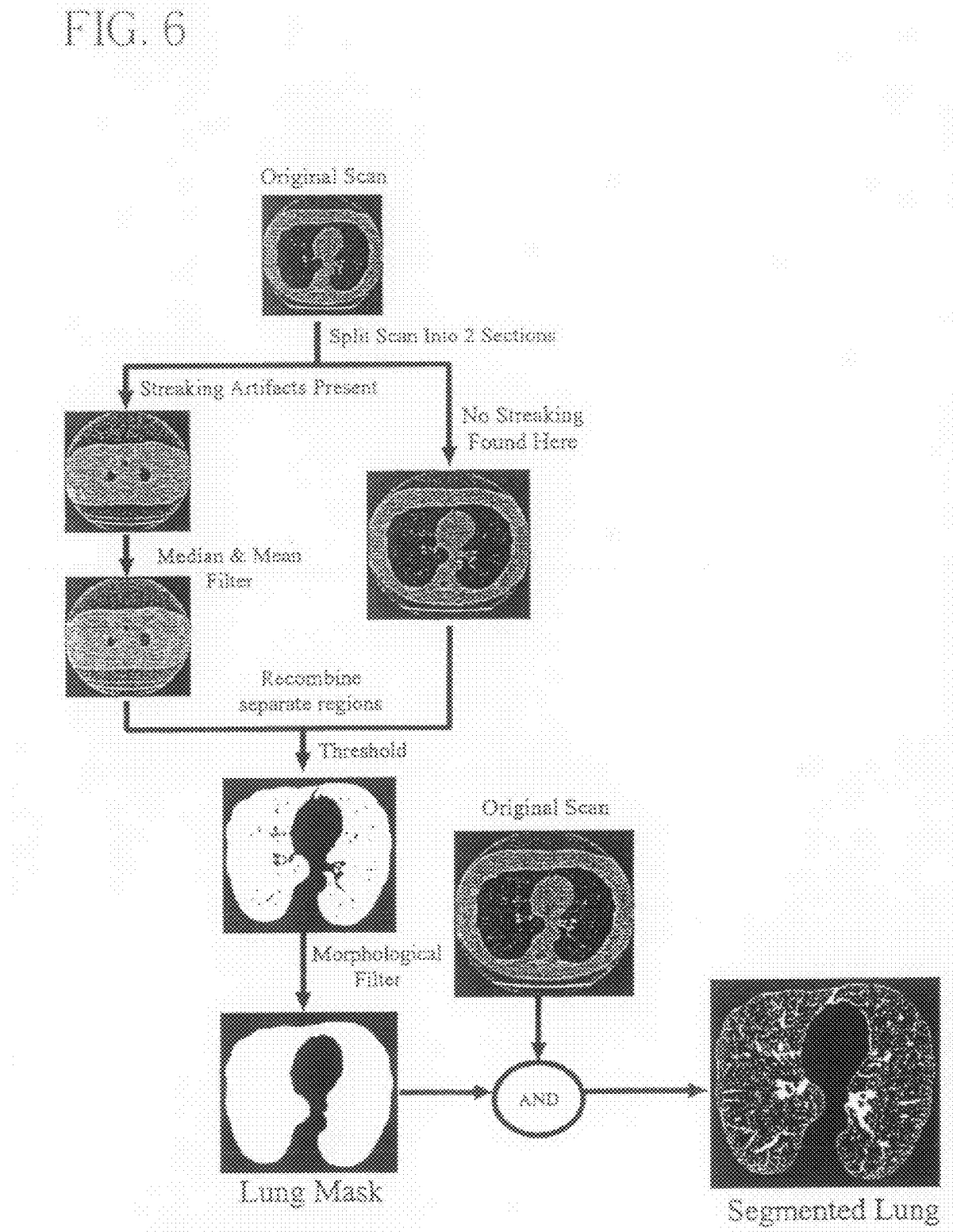
FIG. 6 is a flow chart of the lung segmentation algorithm with sample images incorporated therein.

The segmentation algorithm consists of creating a mask representing the lung volume and applying an AND operation between the mask and the original image. The algorithm for creating the mask is set forth in FIG. 5, and FIG. 6 outlines these steps graphically while the motivation behind this routine is described in detail in the following sections.

The main object of image filtering is to remove the streaking artifacts on the first 25% of the slices due to x-ray beam hardening through the shoulders. The streaking artifacts are characteristically horizontal and tend to greatly distort the segmentation. Many of the later steps in this algorithm operate on binary images and are quite susceptible to noise. A combination of both median and mean filtering reduces the noise significantly. Median filtering preserves the edges around the chest cavity while eliminating much of the streaking effect. Since the streaks are horizontal, a small vertical mean filter will blur the streaking regions, further reducing their effect. This filtering stage is used only to generate a clean image for the mask as the original pixel values are retained in the final segmented lung image.

Figure 9:
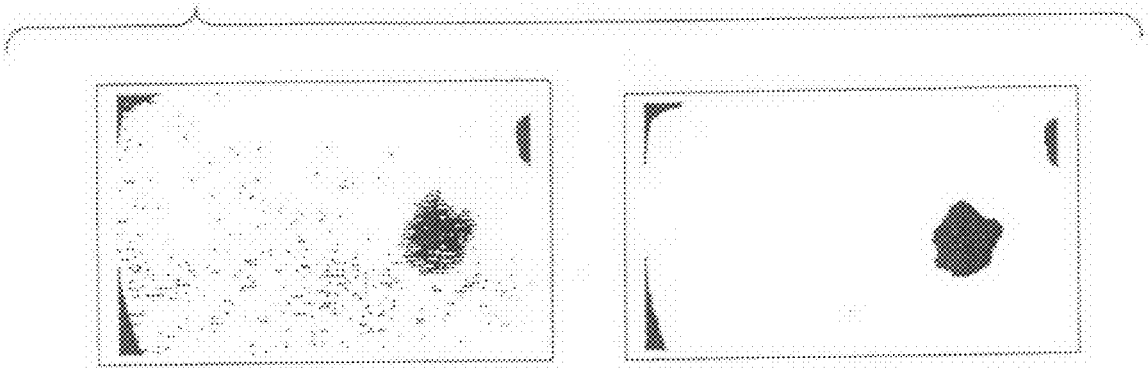
FIG. 9 illustrates on the left hand side a lung after thresholding without median and mean filtering and on the right hand side the image after median and mean filtering.

Experiments have shown that a median filter size of 4×4 produce the best results. Smaller filters did not reliably eliminate noise caused by the streaking artifacts. Further experiments have shown that a mean filter size of 1×3 produces excellent results. The results of filtering are shown in FIG. 9, but the importance of this step is seen more clearly in FIG. 7 after the thresholding operation. The filtering is preferably performed on 2 dimensional slices rather than 3D volumes.

On large data sets, such as full chest CT scans, median filtering is a time consuming operation. To speed up the algorithm, it is important to note that the streaking artifacts appears only at the beginning of the scans. Preferably the median filter for the first 25% of the slices is only computed to reduce the computation time of this stage by 75%. The mean filter is much smaller (1×3) and the computational gains of only running it on part of the image are insignificant.

Most of the segmentation is performed by a simple threshold operation. A seen in FIG. 2, the distribution of intensities of lung parenchyma and solid tissue is bimodal. A simple threshold of 500 can therefore be applied to the entire image. For the most part, this will separate the image into 2 regions: (1) solid tissue and (2) everything else. Included in "everything else" are the lungs, trachea, air surrounding the body, and black background outside of the field of view. By filling in all pixels which touch the image border and inverting the image, the lungs are clearly segmented from the chest cavity, as shown in FIG. 8.

As seen in FIG. 2 and the table in FIG. 3, there is some overlap between the intensities of structures in the lungs and the intensities of solid tissue outside the lungs. Specifically, there is significant overlap in the range between gray levels of 550 and 800. It is therefore impossible to threshold out the ribcage and keep all the vessels, as seen in FIG. 8.

FIG. 9 illustrates the effect of thresholding both with and without image filtering. The noisy image on the left shows the result of thresholding without filtering and the segmented image on the right shows the result of thresholding after filtering.

Up until this stage in the algorithm, any regions with similar characteristics to the lungs will be preserved. This includes air and gas found within the body. This also includes random noise in the background (i.e., outside the thorax) which was not removed by image filtering and thresholding. Selecting only the largest component(s) in the image, we will eliminate minor air pockets and all stray noise which is prevalent throughout the images.

Figure 10:
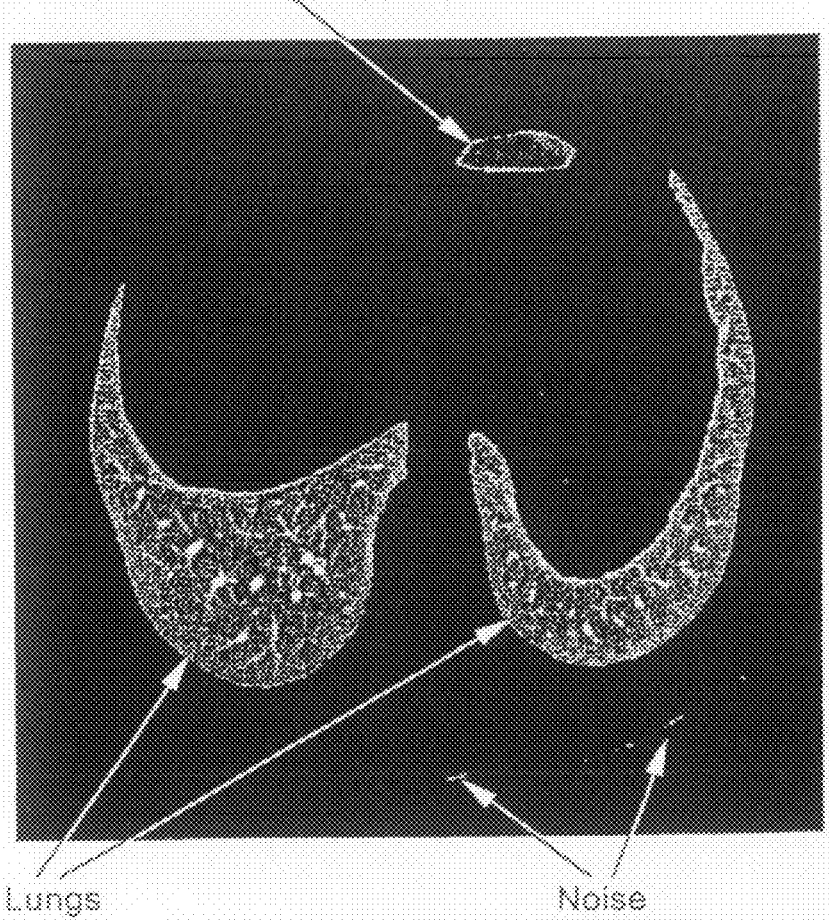
FIG. 10 illustrates two lungs, gas, and some noise, and that the retention of only the largest components would eliminate the unwanted regions.

FIG. 10 shows a region which is removed by retaining only the largest component(s) and discarding all other structures. To perform the selection, preferably all regions with volumes greater than 1% of the total number of pixels are chosen in the image, as explained in S. Hu, E. A. Hoffman, and J. M. Reinhardt, "Automatic Lung Segmentation for Accurate Quantitation of Volumetric X-Ray CT Images," *IEEE Transactions on Medical Imaging*, Vol 20, No 6, June 2001, which is incorporated herein by reference.

Figure 11:
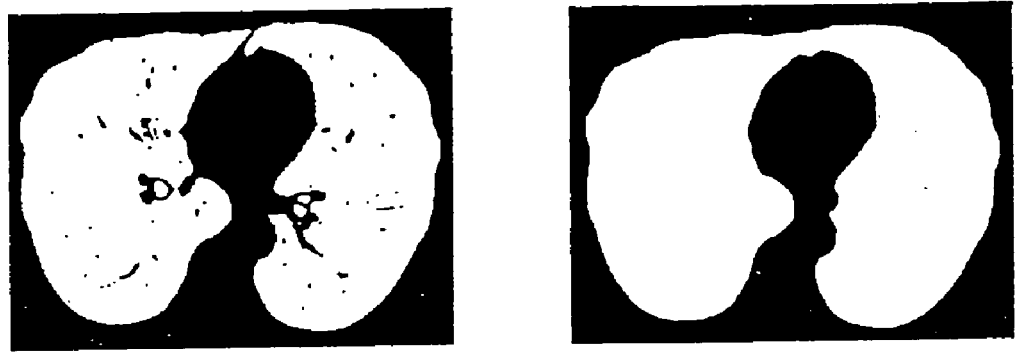
FIG. 11 illustrates at the left hand side a segmented lung after thresholding but before morphological filtering, and at the right hand side the lung after morphological closing.

As previously mentioned, the thresholding operation will segment out blood vessels along with the ribcage, resulting in holes and splotches in the lung region, as seen in FIG. 8. These can be filled in using a morphological filtering operation. By performing a closing, which consists of a dilation followed by an erosion, the spotty regions and holes within the lungs can be removed. Some of the vessels and other structures are quite large, necessitating the use of a large closing kernel. The results of morphological filtering are shown in FIG. 11.

Figure 12:
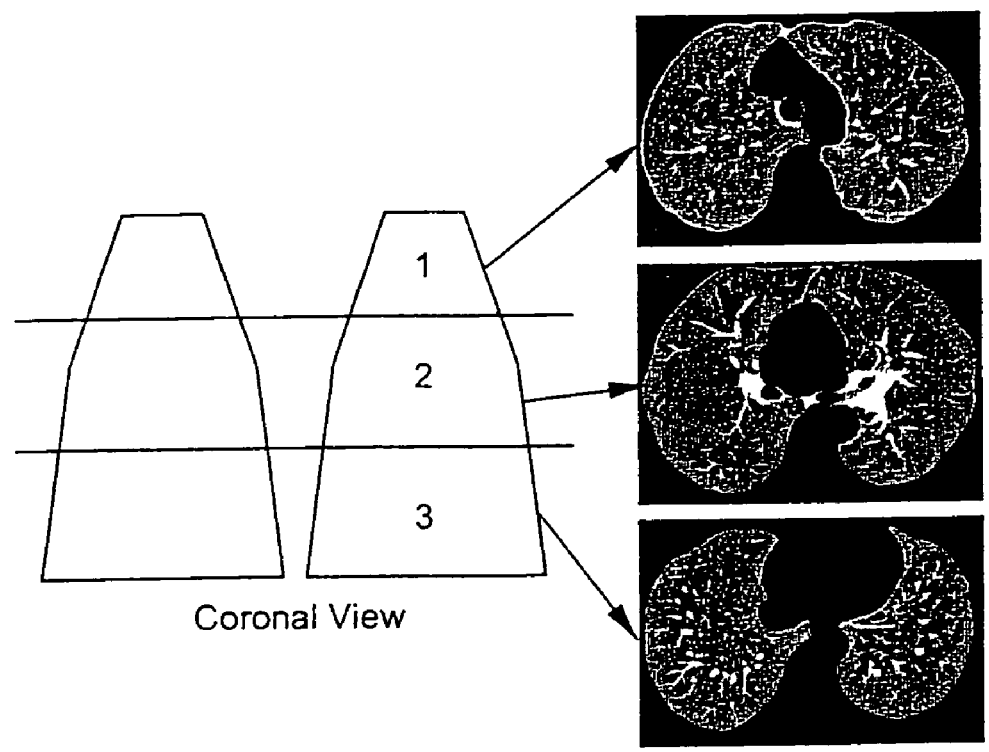
FIG. 12 illustrates the lungs being divided medially into three regions where large vessels are found in region 2 which require a large structuring element, and that only small vessels are found in regions 1 and 3.

Morphological filtering with large structuring elements is computationally expensive. Fortunately, large structures that require a large filter kernel only occur in the middle third of the slices of the lungs. Therefore, the lungs can be divided axially into three distinct regions 1, 2, and 3 as shown in FIG. 12.

As the slices corresponding to each region show, preferably a small structuring element is used in regions 1 and 3 where only small vessels occur, and a larger one is used in region 2, where large vessels are found. Specifically, a large 2D circular filter is preferably used in region 2 (typically 28 pixels in diameter) and filter of half the diameter is used in regions 1 and 3. Referring now to FIG. 13, a table that shows timing trials using a varying kernel size versus using a fixed large kernel for the entire image. In this experiment, a circular filter of diameter 28 was used as the fixed kernel size. This was compared to using the same kernel in region two and reducing it to a diameter of 14 in regions 1 and 3.

Once the binary mask of the lungs is generated, a simple AND operation with the original CT scan will yield the segmented lungs. Finally, the image is clipped such that the new bounding box is just large enough to contain the lungs.

B. Lung Volume Measurements

This section discusses the algorithms used for lung volume measurements. First the motivation behind measuring the lung volume will be explained. Next, a model of the lung will be presented, followed by the algorithm for calculating the volume.

Once the lung has been properly segmented, the volume of both tissue and air in the lungs can be calculated. The objectives of this research are as follows:

1. Accurately measure lung volume.
2. Determine both the inter-patient and intra-patient variation in lung volume.
3. Explore the effects of inspiration on CAD algorithms.
4. Compensate for any effects discovered in (3).
5. Measure the relationship between cross-sectional area of the lungs and entire lung volume.

Once statistics of the lung volumes have been compiled the effect of inspiration on nodule volume measurements will be studied. A positive correlation between lung volume and nodule size in a large set of repeat scan will determine if such a relationship exists. It is also important to note that full chest scans are not always performed during a repeat examination. Typically, a high resolution scan of the suspicious region is performed. Such scans contain only a few cross-sectional slices of the region of interest. Therefore, the relationship between 2D cross-sectional area and inspiration must be explored.

The lungs can be modeled as containing air with a gray level value of zero, and tissue with a gray level value of 1000. All intensity values in between that range must be a combination of air and tissue, confounded by the partial voxel effect. Based on this assumption, a gray level of 500 represents a volume comprised of ½ air and ½ tissue. Equation 1 depicts this formally, where V is volume and I is intensity.

$$V_{air/voxel} = \left(1 - \frac{I_{voxel}}{I_{tissue}}\right) * (V_{voxel}) \quad (1)$$

For example, a gray level of 250 represents 25% tissue and 75% air. If the image resolution is 0.5 mm×0.5 mm×2.5 mm per voxel, the volume of a voxel is 0.625 mm$^3$ and the volume of air in that voxel is 0.156 mm$^3$.

Figure 14:
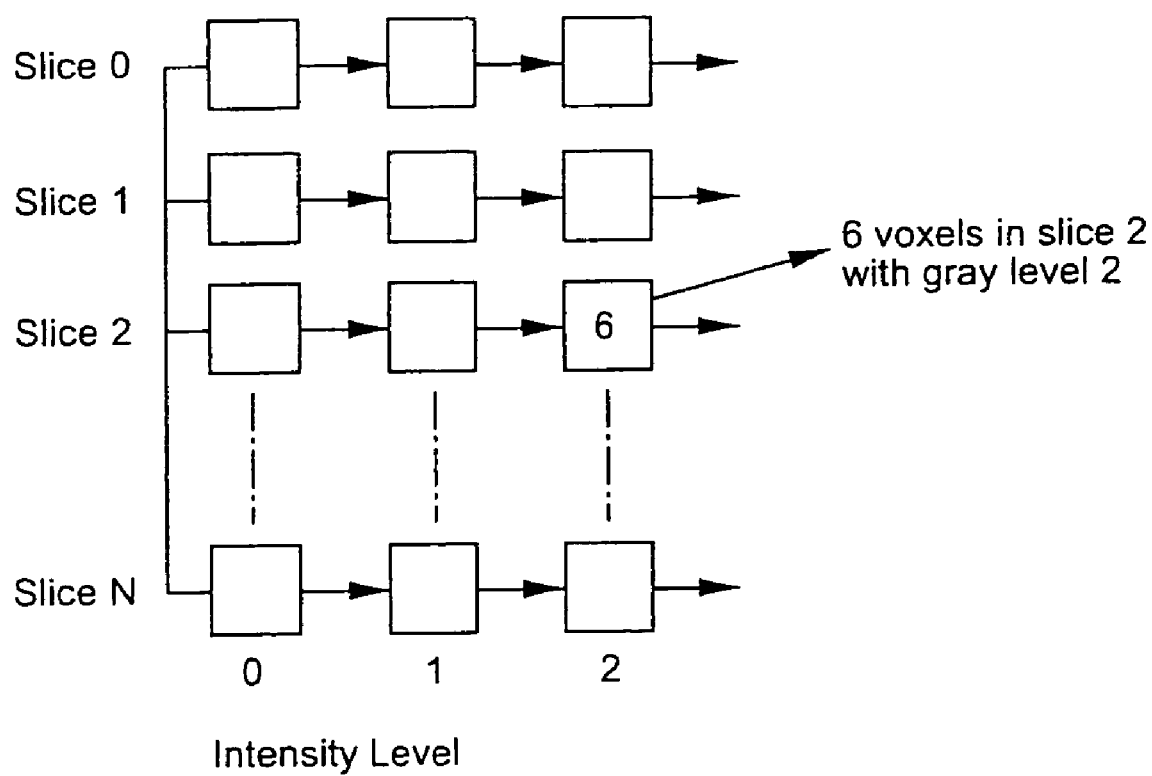
FIG. 14 illustrates a matrix containing the histograms of the segmented lung slices.

Referring now to FIG. 14, a matrix is generated from the segmented lung image in which each column represents a gray level value and each row represents a slice in the scan to perform this analysis. The entries in the matrix are the number of times that a particular gray level appears in that slice of the image. This data structure is simply a histogram of the image, separated into slices. With such a structure in place, it is easy to perform and repeat the volume measurements on both the full lung volume and on an individual slices.

To calculate the volume in the lungs, the number of voxels in the segmented image is counted and multiplied by the volume of each voxel. This represents the volume of the entire lung. This can be performed quickly using the histogram because the counting has already been completed. Using the model described above, that each voxel is part air and part tissue, the sum of "tissue voxels" multiplied by the volume of a voxel equals the amount of tissue in the lung. The equations for calculating the volume of the lungs and the volume of the tissue in the lungs are as follows:

$$V_{Lung} = \sum_{s \in S} \sum_{i \in I} L[s][i] * V_{voxel} \quad (2)$$

$$V_{Tissue} = \sum_{s \in S} \sum_{i \in I} \frac{i}{I_{tissue}} * L[s][i] * V_{voxel} \quad (3)$$

where V represents volume, I represents voxel intensity, and $L[s][i]$ is the number of pixels of intensity i in slice s of image L.

Often times with repeat scans, only a high resolution scan of the region of interest is acquired. As a result, full lung volumes are not always available to measure the amount of inspiration in repeat scans. As a solution, the area of single axial CT images from two scans may be used to estimate the variation in inspiration between the two. The histogram data structure described above can be used to calculate the cross-sectional area of a single slice. Given the volume of the 2 entire lungs, it may be possible to relate the cross-sectional area of each to the volume of the entire scan.

The lung segmentation algorithm was run on 196 individual chest scans and 24 pairs of repeat scans from a Cornell University ELCAP database. Out of the 196 scans, 115 contained 2.5 mm slices and 81 contained 5 mm slices. The 24 pairs of repeat scans consisted of 19 5 mm scans and 5 2.5 mm scans. Repeat scans of different reconstructions were not considered. In-plane resolution varied between 0.54 mm/pixel and 0.79 mm/pixel.

Images were acquired on a either a General Electric® LightSpeed™ or HiSpeed™ Helical CT scanner. X-ray tube current ranged from 40-200 mA and the tube potential was either 120 or 140 kVp. Testing is preferably performed on a dual-processor 700 MHz computer. The algorithm ran in approximately 6-8 minutes on a full lung scan with 2.5 mm contiguous slices. Without using the varying filter sizes as described above, the algorithm ran in about 14-15 minutes.

C. Finding Location and Size of Pulmonary Nodule

Given an initial seed point inside the nodule, an algorithm finds the center location of the nodule and the radius of the sphere circumscribing the nodule. The following subsections describe the algorithm and choices of functions.

The algorithm is provided a candidate location that is some seed point P, which is within the nodule in the image, and a starting radius r and delivers the optimal location P' and radius r' of the nodule. The algorithm for finding the location P' and radius r' of the nodule is shown in FIG. 15. The value of r is incrementally increased and for each value of r the best location of the nodule center P is computed. A new location is calculated by maximizing the correlation (or the response) between the image and a locater template function. The template function is chosen so that the maximum response is given when the template is centered over a nodule with radius r as discussed further below. Thus, maximizing the correlation yields the most likely location of a nodule with the current radius.

The algorithm determines the radius of the nodule by terminating itself at the appropriate iteration. Another template function, centered at P, is applied to the image at the end of each iteration. The sizing template function is designed so that its value decreases dramatically when the radius of the function has become larger than the radius of the actual nodule. Thus, when there is a large decrease in the value of the second template function, the radius of the actual nodule has been exceeded and the algorithm terminates and returns the location and radius from the previous iteration.

The nodule finding algorithm was developed assuming a two level model where the nodule, blood vessels, and pleural wall are all a single high intensity, while everything else is a single low intensity. The template functions use parameters of location and radius. The radius does not refer directly to the size of the template function. Rather, the radius is a parameter that describes the size of the nodule for which the template will detect; meaning that the template does not necessarily need to be zero past the extent of the radius The locater template functions is designed to locate the approximate center of mass of a nodule (for nodules attached to the pleural surface a repeatable central location is obtained since the location of the actual center of mass is not knowable). The function has four parameters: the center in x, y, and z, and the radius. In the algorithm, the radius is fixed at each iteration, but the center of the template can move. The locater template function was designed, with a given radius, so that it is maximized when the function is centered over a nodule of the same radius.

Figure 16A:
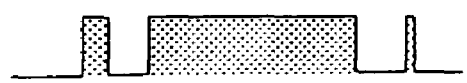
FIG. 16 illustrates a one dimensional model of a) isolated nodule next to blood vessels, and b) a nodule attached to the pleural wall.
Figure 16B:
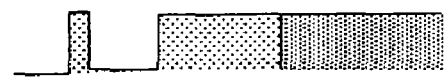
Figure 17A:
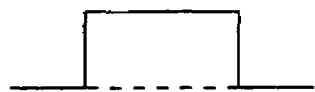
FIG. 17 illustrates locator template functions.
Figure 17B:
Figure 17C:
Figure 17D:
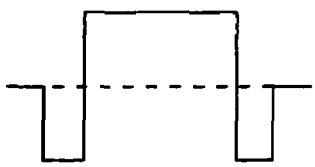
Figure 17E:
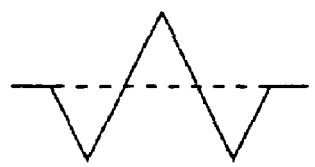
Figure 17F:
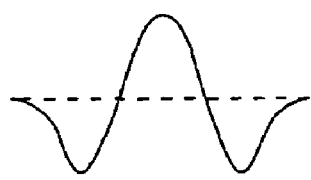

Consider a 1-D example where an isolated nodule is modeled as a large region of high intensity. FIG. 16A shows an example model where the nodule is the center shaded region, while the outer regions consist of noise (composed of high-intensity objects like vessels).

Figure 18A:
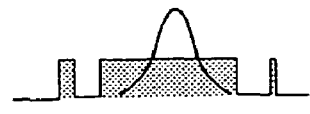
FIG. 18 illustrates one dimensional examples of the maximizing locations of template functions for (a-c) a Gaussian template on an isolated nodule, (d-f) LOG template on a nodule on the wall, and (g-i) LOG template on an isolated nodule.
Figure 18D:
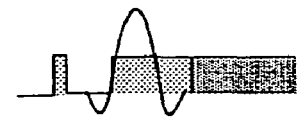
Figure 18G:
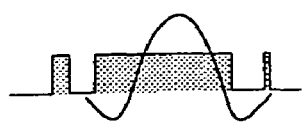
Figure 18B:
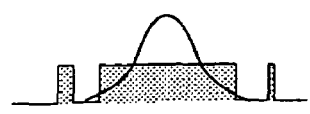
Figure 18E:
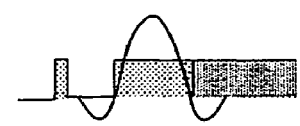
Figure 18H:
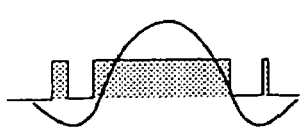
Figure 18C:
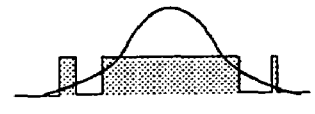

Consider some simple 1-D template functions shown in FIG. 17. The square template function, FIG. 17A, biases everything equally, causing the template to be very sensitive to noise in the periphery. The sensitivity to noise can be reduced by tapering the template function to be shaped like a triangle, FIG. 17B, or a Gaussian, FIG. 17C. The large values near the center will keep the function centered over the high-intensity region of the nodule, while the lower values further from the center will diminish the effect of any other high-intensity objects. FIGS. 18A through 18C illustrate where the Gaussian template function will be maximized for cases where the size of the function is smaller, the same size, and larger than the size of the nodule.

Now consider a 1-D model of a nodule attached to the pleural wall, shown in FIG. 18B. The nodule is the lightly shaded central region, the pleural wall is the darkly shaded region on the right, and the lightly shaded region on the left is some noise (blood vessel). Although shaded differently, note that the nodule and the pleural wall are at the same intensity level. With this model, the Gaussian template function will fail to perform correctly. The template does not prevent itself from slipping into the wall and centering itself over the combination of the nodule and the wall.

Figure 18F:
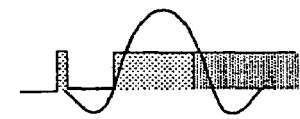

Nodules on the pleural wall can be located by choosing a function that forces itself away from the wall. This can be achieved by using a function that has positive values within the radius of the function and negative values outside the radius, like FIGS. 17D through 17F. Two examples of this type of function are the Laplacian of the Gaussian (LOG) and the difference of Gaussians (DOG). When maximizing the response of the template function, there are two forces fighting against each other. The positive portion of the template function will try to keep the function centered over the high-intensity regions. Countering this, the negative portion of the template will try to push the template away from the high-intensity regions, resulting in an equilibrium along the edge of the high-intensity region of the nodule. FIGS. 18D through 18F show how the LOG-like template function should behave on the 1-D model of a nodule on the wall. If the total weights, the distribution, and the sizes of the positive and negative regions are balanced correctly, then the LOG-like template function should behave accordingly.

Figure 18I:
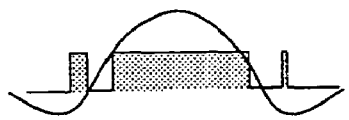

The LOG-like template function can also be used on isolated nodules. The positive region of the template function will stay near the center of the nodule, while the negative regions will force the function away from any noise in the periphery of the image. FIGS. 18G through 18I show how the LOG-like function will behave when applied to the 1D model of an isolated nodule. When the size of the template is smaller than the nodule, the template will hug the edge of the nodule and when the positive region of the template is larger than the nodule, it will be centered over the nodule.

Figure 19:
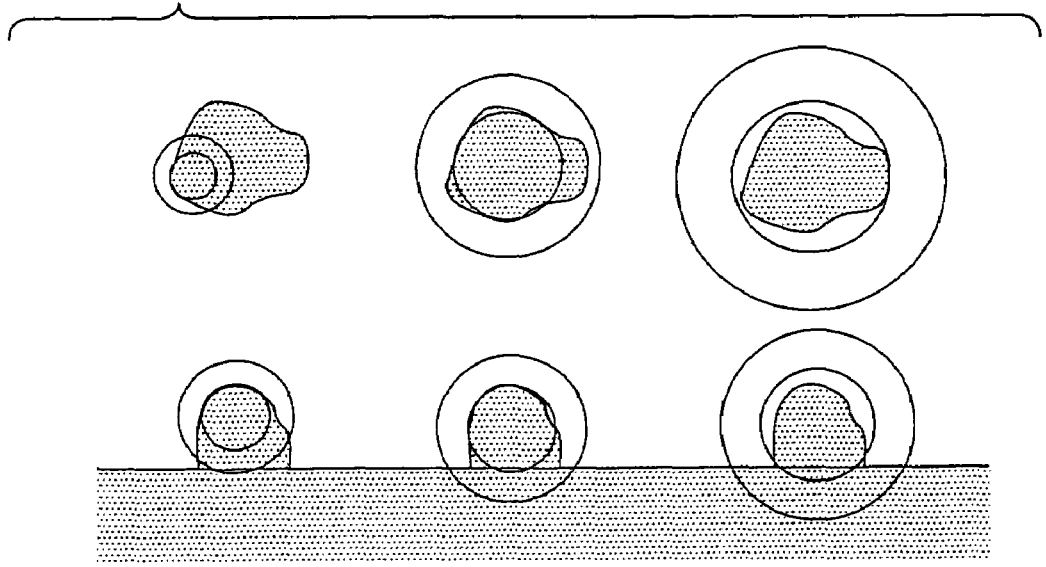
FIG. 19 illustrates two dimensional examples of the maximizing locations for two dimensional LOG templates of various radii on isolated and pleural nodules where the inner and outer circles represent the positive and negative regions, respectively, of the LOG template.

The above illustrates the preferred behavior of the locator template function for the 1D model of an isolated nodule and a nodule on the wall. The model is now extended into two and three dimensions. For the 2D case, the 1D LOG-like function is extended into two dimensions. The template now consists of two circular regions; the smaller region contains positive values and the region outside the smaller region contains negative values. FIG. 19 shows a few examples of how the 2D template function is expected to behave for isolated and pleural nodules. For the 3D case, the locater template function will have spherical regions with an analogous distribution as the 2D and 1D cases.

One thing to note about the locater template function is that it does not need to have a constant total weight for different radii. The algorithm does not maximize the locater template function throughout all the iterations and all the radii; instead, it is maximizing the template function for a fixed radius in each iteration. Thus, the template is not required to have a constant weight for different radii. It should suffice to only maintain the proper scaling between the sizes and the distribution of the template regions.

The sizing template function is used to indicate when the radius of the function is equal to the size of the sphere circumscribing the real nodule. The sizing template function uses the radius during the current iteration and the location of the candidate nodule, determined by the locater template function. After each iteration in the algorithm, a value is calculated using the sizing template function. Two preferred methods for determining when the algorithm has found the location and size of the nodule in the image are discussed below.

Figure 20:
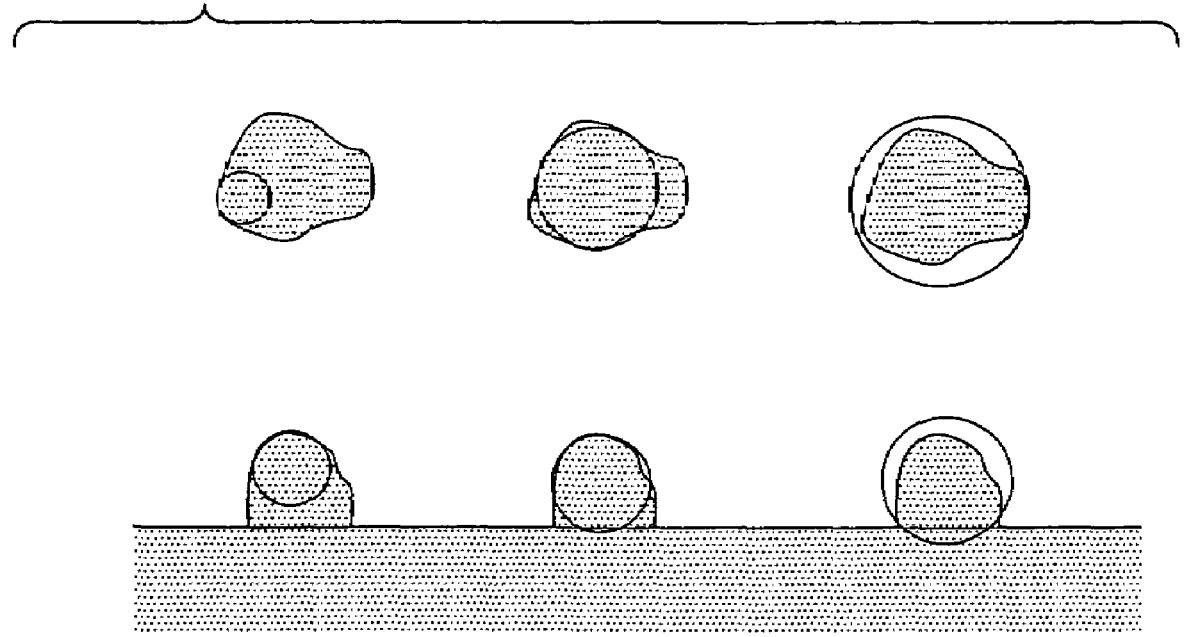
FIG. 20 illustrates two dimensional examples of a sizing template function of various radii which exhibit dramatic changes in the distribution of values inside the circle when the sizing template function becomes too large.

The first method is to look for a large change in the response of the sizing template function. Using the LOG-like locater template function, the positive region, the inner circle, is expected to be overlayed on the high-intensity values of the nodule. As the radius of the template function increases, the positive region will remain within the nodule. This is illustrated in FIG. 20. Eventually the positive region will become larger than the nodule and there will be a sharp decrease in the response of the sizing template function between iterations of the algorithm. To find this stopping criterion, a sizing template function is chosen so to be a mean filter shaped like a sphere. When the sphere becomes larger than the nodule, the distribution of values inside the sphere changes, causing the response of the template function to change dramatically.

Figure 22:
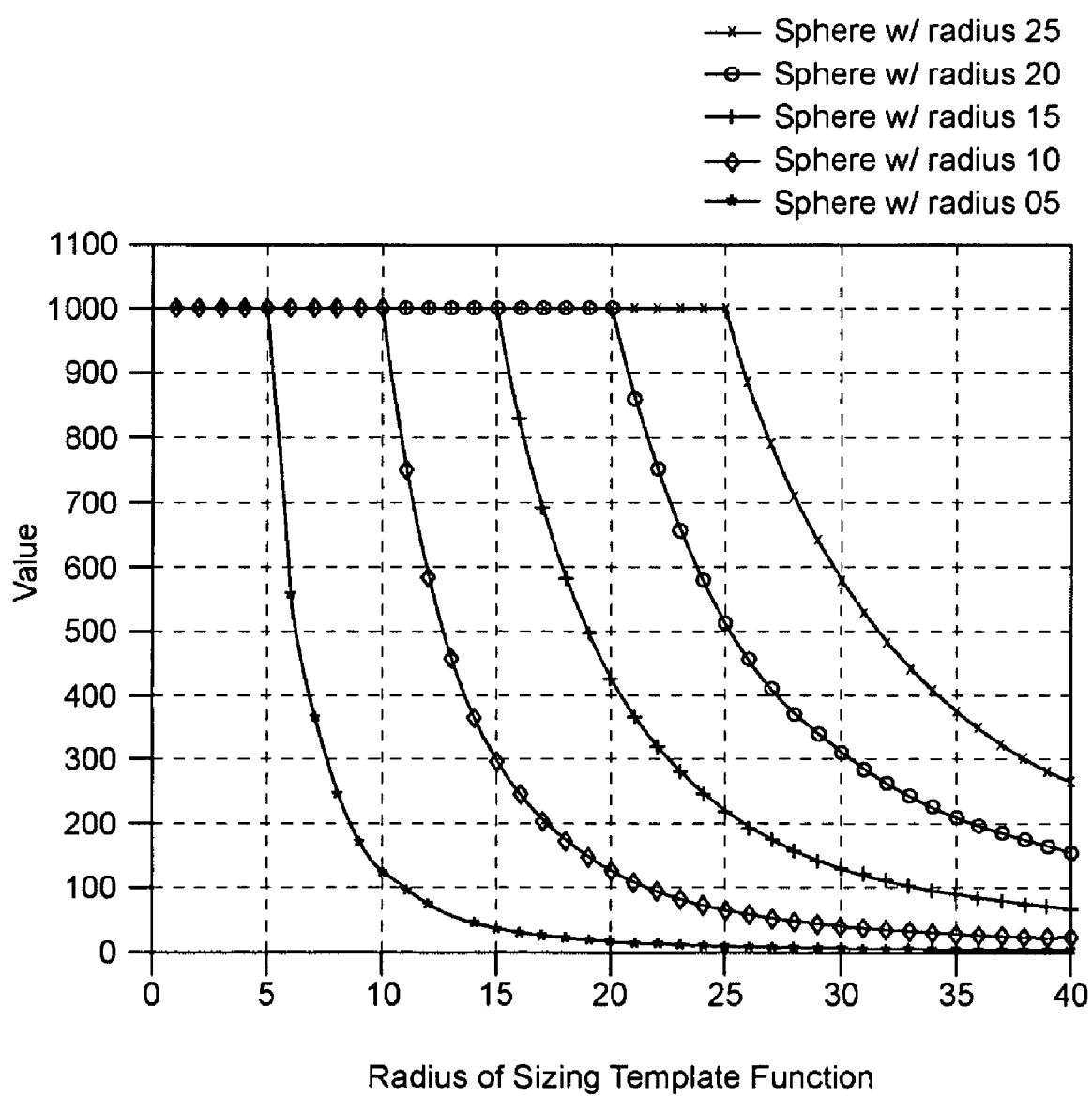
FIG. 22 illustrates a response of the mean filter function for various sized spheres (solid intensity of 1000) versus the radius of the template function.

FIG. 22 shows the response of the mean filter function to various sizes of ideal nodules (spheres of intensity 1000). For the ideal nodule, the response of the filter function is constant until the radius of the filter function exceeds the radius of the ideal nodule. When this happens, the response of the filter quickly decreases.

The second method of finding the size of a nodule is to design the sizing template function so that it has a specific response when the template function is the same size as the real nodule. For example, if a 3D Gaussian function, where the standard deviation is equal to the radius, has the response shown in FIG. 23. When the response of the Gaussian template is 200, the radius of the Gaussian is the same as the radius of the nodule, thus providing a stopping criterion for our algorithm.

One very important property of the sizing template function is that it must have a constant total weight regardless of the size of the template. This property will insure that the response of the template will be consistent between different sizes of nodules.

The implementation of the algorithm will now be discussed. This will include a more detailed description of the algorithm, a mathematical definition of some template functions, calculation of the initial seed point, introduction of two search methods for the maximization of the locator template function, quick function evaluations, and the termination criterion.

A detailed description of the algorithm is shown in FIG. 21. The algorithm is modified so that it terminates when the response of the sizing template function is within E of the target value. This feature is added to the algorithm so that the radius does not go too far past the actual radius of the nodule.

The algorithm takes in a 3d CT image of a nodule. First, the image is clipped at intensities over 1000. This is done to minimize any affect that the very-high intensified bone will have on the algorithm.

The next step is to define the locator and sizing template functions. The template functions are preferably either the Gaussian, the Laplacian of the Gaussian, or the difference of Gaussians. The template function has four parameters, (sx, sy, sz, σ), which correspond to the x-location, y-location, z-location, and radius. The initial location is either calculated from the image or specified by the user, and depending on the type of sizing template function, the target response value is set.

Starting with the initial conditions, a radius of 1, and a radius step-size of 1, the algorithm finds the best locator template response by using a search method to move the center of the template function. Preferably the search method is a hill-climbing method as discussed below. Once the maximum value is found for the given radius, the radius is increased by the radius step-size and the search is repeated using the current location as the starting point.

At each iteration the response of the sizing template function, γ is calculated. The algorithm iterates until the sizing response is less than the target value. If γ is within ε of the target, then the algorithm is finished. Otherwise, the algorithm backtracks by setting the location and radius parameters to their values in the previous iteration, dividing the radius step by two, and repeating the search procedure.

Finally, after the target value is reached within ε, or the radius step-size is smaller than some α, the search process terminates and the current parameters are the location and radius of the nodule.

The template function is a function of four parameters: the center (location) of the template, (sx,sy,sz), and the radius of the template, σ. The response of the template function is calculated by taking the correlation between the image im and the template M as in Equation (4).

$$\Gamma(sx, sy, sz, \sigma) = \sum_{x, y, z} \sum \sum im(x, y, z) * M_{sx,sy,\sigma}(x, y, z) \quad (4)$$

The locater template function is designed to produce the largest response when the kernel is centered over the target object. Thus, by maximizing this function at each iteration of the nodule finding algorithm, the best candidate for a nodule of radius r is found. There are many types of functions to choose from, but the preferred functions are the Gaussian, the Laplacian of the Gaussian, and the Difference of Gaussians.

Figure 24:
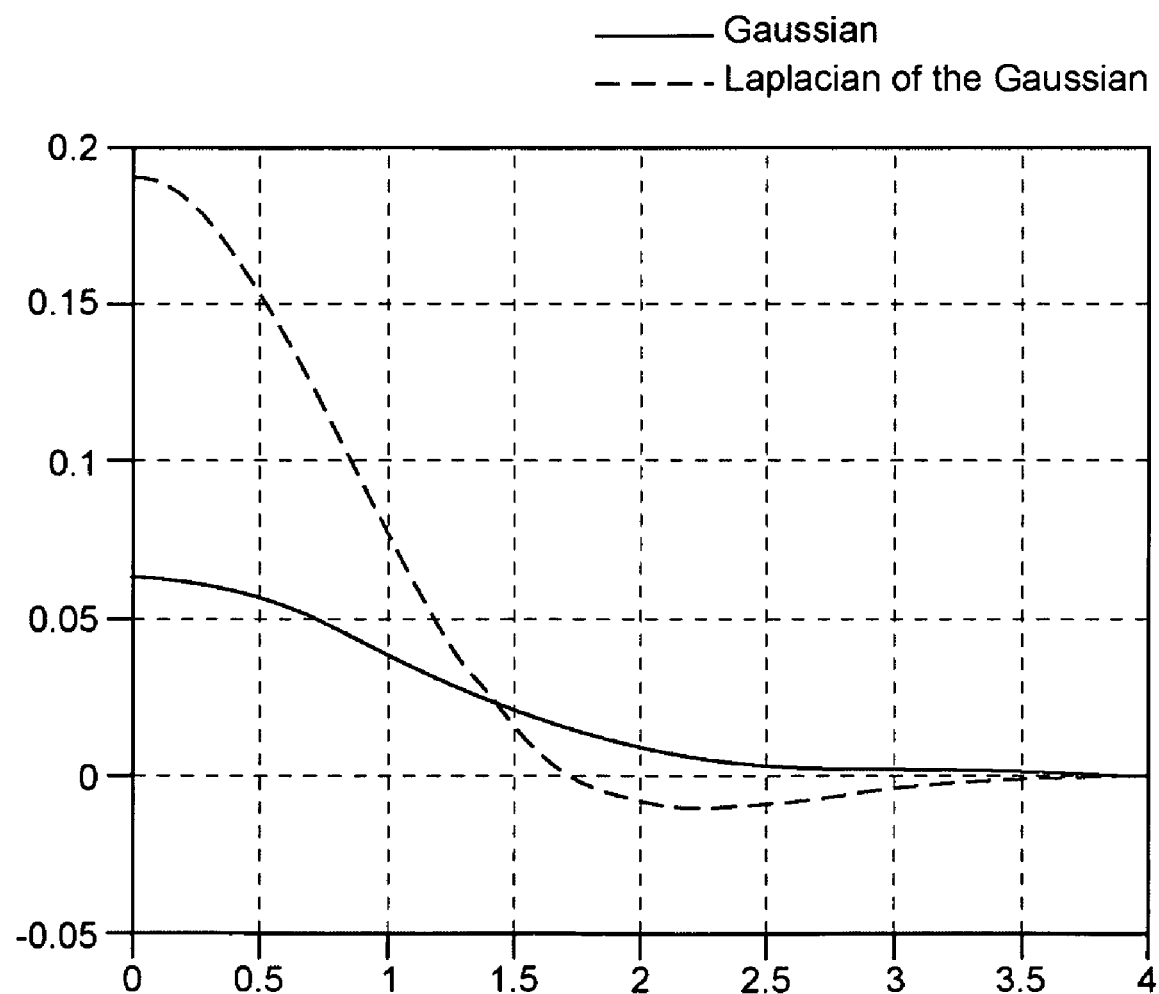
FIG. 24 illustrates a graph of the Gaussian and the Laplacian of the Gaussian.

The 3D gaussian is a strictly positive symmetric function defined by Equation (5). The Gaussian function can be used to find nodules when the pleural surface is not present in the image. The metric function will have its highest value when it is centered over the nodule. A graph of the Gaussian is shown in FIG. 24.

$$G_{sx,sy,sz,\sigma}(x, y, z) = \frac{1}{\sigma^3 (2\pi)^{3/2}} e^{\frac{-((x-sx)^2 + (y-sy)^2 + (z-sz)^2)}{2\sigma^2}} \quad (5)$$

The Laplacian of the Gaussian (LOG) is defined in Equation 7. This function has a positive weight close to the center and a negative weight further out, as seen in FIG. 24. This function is useful in locating nodules on or near the pleural surface. The positive interior will latch onto the nodule, while the negative exterior will keep the kernal from moving towards the wall. In the algorithm, the LOG has the disadvantage that the initial location must be within the nodule. Otherwise, the negative weight of the exterior will cause the LOG to grow away from the nodule.

$$LOG_{sx,sy,sz,\sigma(x,y,z)} = -\left[\frac{\partial^2}{\partial x^2} + \frac{\partial^2}{\partial y^2} + \frac{\partial^2}{\partial z^2}\right] G_{sx,sy,sz,\sigma}(x, y, z) \quad (6)$$

$$= \frac{1}{\sigma^2}\left(3 - \frac{x^2}{\sigma^2} - \frac{y^2}{\sigma^2} - \frac{z^2}{\sigma^2}\right) * G_{sx,sy,sz,\sigma}(x, y, z) \quad (7)$$

The Difference of Gaussians, given in Equation (8), is similar to the Laplacian of the Gaussian in that they both have positive and negative regions. However, changing the $\sigma_1$, $\sigma_2$, $m_1$, and $m_2$ values will lead to different sizes and weights of the two regions, allowing for a more customizable template than the LOG.

$$DOG_{sx,sy,sz,\sigma}(x,y,z) = m_1 * G_{sx,sy,sz,\sigma_1}(x,y,z) - m_2 * G_{sx,sy,sz,\sigma_2}(x,y,z) \quad (8)$$

The initial seed point should be somewhere within the nodule in the image. This may be provided by user input, or it can be estimated from the image. A simple way to calculate the initial location would be to use the center of the image:

$center_x = im.xlo + (im.xhi - im.xlo + 1)/2$ $center_y = im.ylo + (im.yhi - im.ylo + 1)/2$ $center_z = im.zlo + (im.zhi - im.zlo + 1)/2$ When using the Gaussian for the locator template function this may be fine, but when using the LOG or DOG functions the initial starting location must be within the nodule. For these functions, the center of mass (COM) of the image is preferred for setting the initial conditions. The COM is calculated by first thresholding the image at half of the largest pixel value in the image and then calculating the center of mass using the standard equations:

$$COM_x = \frac{\sum_{i,j,k} \sum \sum im(i, j, k) * i}{\sum_{i,j,k} \sum \sum im(i, j, k)}$$

$$COM_y = \frac{\sum_{i,j,k} \sum \sum im(i, j, k) * j}{\sum_{i,j,k} \sum \sum im(i, j, k)}$$

$$COM_z = \frac{\sum_{i,j,k} \sum \sum im(i, j, k) * k}{\sum_{i,j,k} \sum \sum im(i, j, k)}.$$

The method used to search for the optimal nodule location has a major impact on the running time of the algorithm. Any kind of fancy search procedure could be used, but this is not necessary for this application. From iteration to iteration the new optimal location will not deviate much from the previous optimal location. Since the previous optimal location is used as the starting point for each search, the search method will not have to look very far for the maximum in the search-space.

Fancy search methods, such as Powell's method described in W. Press, *Numerical Recipes in C*, 2nd Edition, Cambridge University Press, 1992, which is incorporated herein by reference, are usually less efficient when moving small distances because these algorithms are designed to search a very large space. In other words, they are optimized to tradeoff between the efficiency in moving giant steps and the efficiency of moving in small steps.

In the end, hill-climbing, a greedy search method, is preferred for the nodule finding algorithm because it is more efficient when the optimal location doesn't move very far. The Hill-Climbing is shown in FIG. 25. Using an the initial location and a stepsize, the hill-climbing algorithm evaluates the locator template function for each of the possible 6 moves in parameter-space and then moves in the direction of the largest decrease. The algorithm terminates when there is no move that decreases the metric.

The search procedure requires many evaluations of the correlation between locator template function and the image. These calculations can be costly because the template function usually involve exponentials. Fortunately, in any given iteration of the search procedure, the radius of the template function is held constant. It is possible to save calculations by storing the template function values in a temporary image (the classic engineering dichotomy of time versus space).

The values of the locater template function centered at the origin are stored in a temporary image at the beginning of each search procedure. For the Gaussian and the LOG, values are only calculated out to 3 or 5 times the radius α because the functions converge to zero. Also, the function is only evaluated at positive location points because these functions are radially symmetric, Now when the response of the template function is required, the temporary image is offset by the location of the template function, and the correlation between the image and the temporary image is calculated.

Figure 23:
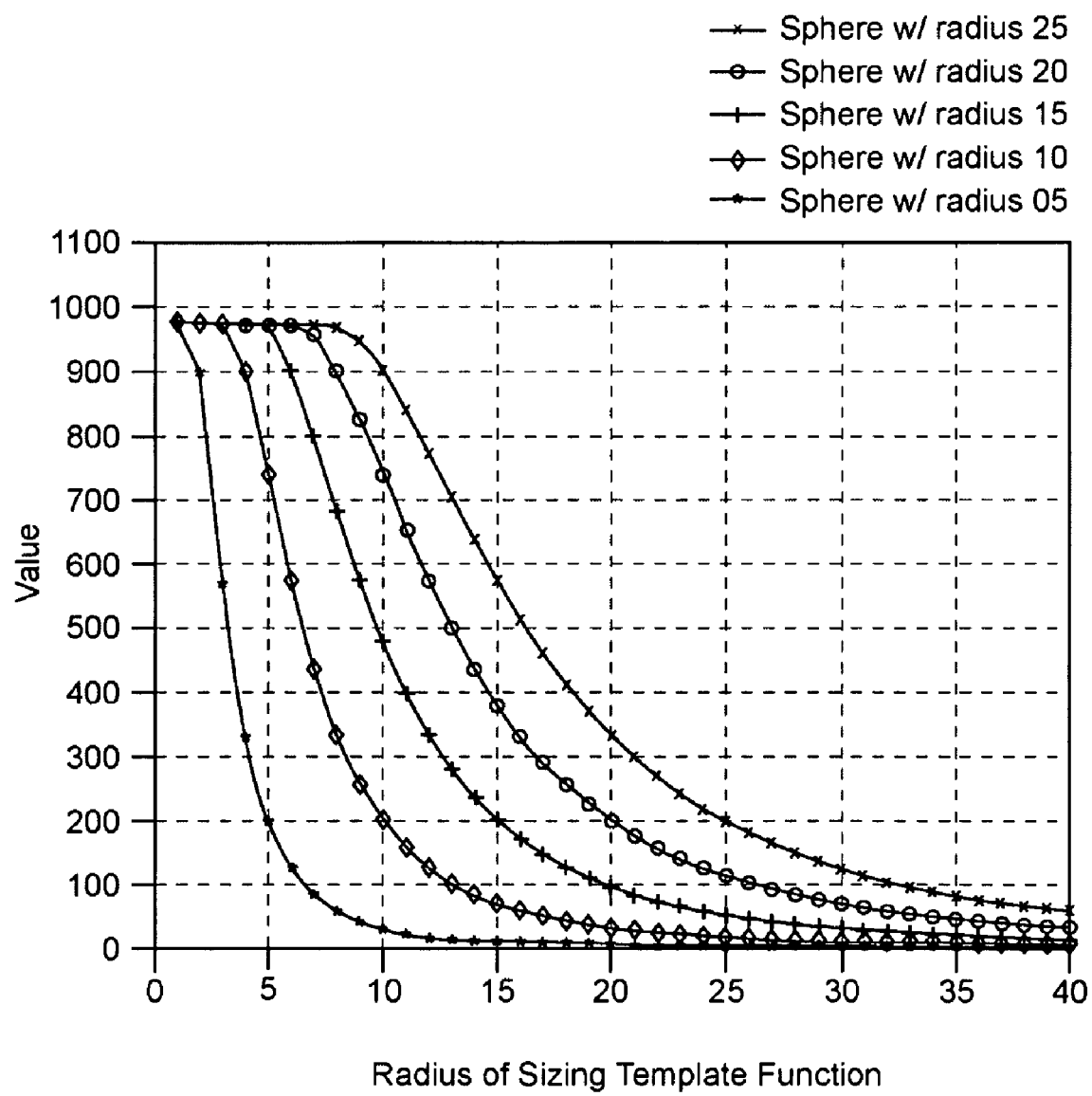
FIG. 23 illustrates a response of a Gaussian template function for various sized spheres (solid intensity of 1000) versus the radius of the template function.

The target response determines when the algorithm should terminate. The target value is chosen such that the algorithm will terminate when the location and radius parameters best circumscribes the nodule. The target value can be found either through an ideal model of a nodule or through experimentation. FIG. 23 shows the response of a Gaussian function to several ideal nodules (spheres) of different radii. In the ideal case, the target response of the Gaussian sizing function should be 200. The best target response has been determined to be 300 by experimentation with a small subset of real nodules from the database. Using a small number (four) of nodules, the response of the sizing function was tracked and the value that causes all the nodules to be circumscribed was selected.

Figure 26:
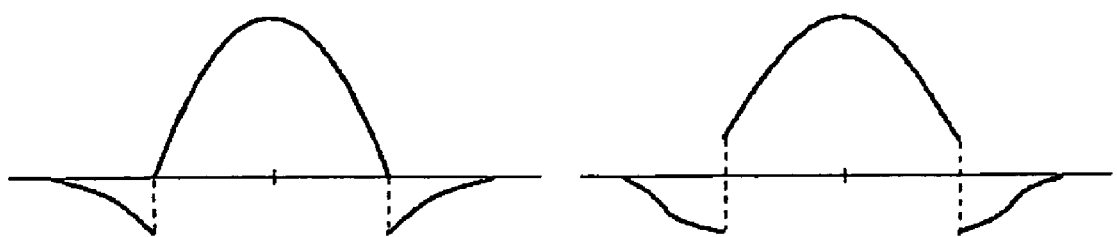
FIG. 26 illustrates locator template functions.

Based upon the experimentation, the locator template functions shown in FIG. 26 will be stable. The large negative values near the border between the positive and negative regions help the template find the edges of the nodule. In addition, the difference of Gaussians (DOG) can be used to correctly balance the weights and sizes of the positive and negative regions in the template so that the template will not slip into the pleural wall The nodule finding algorithm is preferably implemented in the C programming language for a VisionX software package on a FreeBSD system. VisionX software provides computer tools and programs for the analysis and visualization of image data. It is suitable for a wide range of image analysis applications and is designed to address the processing needs of multidimensional image sets that arise both from temporal image sequences and from image modalities that involve three-dimensional data collection.

VisionX software has been used in a wide range of research applications including multispectral image analysis, three-dimensional object recognition, multiframe image analysis, target tracking, neural networks, biological cell analysis, and three-dimensional biomedical image analysis. Important features of the VisionX software include the ability to handle multidimensional image sets, a wide range of available processing functions, and a flexible tagged data format that facilities the automatic recording of the history of a file.

FreeBSD is an advanced operating system for x86 compatible, DEC Alpha, and PC-98 architectures. It is derived from BSD UNIX, which is a version of UNIX developed at the University of California, Berkeley. FreeBSD offers advanced networking, performance, security, and compatibility features. FreeBSD can be installed from a variety of media including CD-ROM, DVD-ROM, floppy disk, magnetic tape, an MS-DOS partition, or if there is a network connection, it can be installed directly over anonymous FTP or NFS.

The nodule finding algorithm preferably inputs a floating point, byte, or short image and outputs the location and size of the nodule. Many options are available, including translation and radius search limits, a choice between search strategies (Hill-Climbing or Powell's method), initial starting location, type of template function, and termination criteria. The program also preferably outputs several types of images for debugging purposes. The program was expanded to allow the algorithm to run on two-dimensional images.

D. Pulmonary Nodule Registration

The algorithm registers pulmonary nodules in 3-d images of high-resolution focused CT-scans. For the most accurate characterization it is important to have images from high-resolution CT scans because these images will better localize the boundaries of the nodule. A rigid-body transformation model is assumed, meaning that in general the structures in the images are confined to simple translation and rotation. In order to simplify the transformation model, an isotropic image-space is also assumed. Using these assumptions, an algorithm was developed to register pulmonary nodules from two different time periods by defining a metric between the two images and performing a minimizing search on the metric.

The algorithm requires two input images, and produces an output that is the first image registered to the second image. The rigid-body registration algorithm is shown in FIG. 27. The two input images, $im_1$ and $im_2$, are converted to floating-point pixel format. Preferably the images are masked to ignore irrelevant pixel data (e.g. bones). Next, the initial conditions for the rigid-body transformation is determined. The metric between two images is defined as a number that represents how closely two images are related to each other. By selecting the appropriate rigid-body parameters, the metric between the second image and the transformation of first image can be minimized or maximized depending upon the registration metric, resulting in the best registration for the given metric.

The first step in the registration algorithm is to perform some pre-processing on the input images. If necessary, the input image is converted from byte or short pixel-formats to the floating point pixel-format.

If mask images are provided, the input images are masked by setting the appropriate pixels to the background value (−1000). Masking an image tells the registration algorithm to ignore certain areas of either image when attempting to perform the registration. This can be useful if a large structure in an image is causing misregistration of the object of interest. By using a mask, the algorithm can be told to ignore the larger structure, thus allowing the object of interest to be registered to itself.

The registration metric is defined as a function of two images, $im_1$ and $im_2$ and six rigid-body transformation parameters, $(t_x,t_y,t_z,r_x,r_y,r_z)$. To calculate the metric, the first image is transformed using the rigid-body parameters, resulting in $im_{1t}$. One definition of the metric value is the correlation between the transformed image $im_{1t}$ and the second image $im_2$, as given in the following equation.

$$C = \frac{1}{N} \sum_{i,j,k} \sum \sum im_{1t}(i,j,k) * im_2(i,j,k) \quad (9)$$
$$im_{1t}(i,j,k) \neq \text{background}$$
$$im_2(i,j,k) \neq \text{background}$$

where N is the number of pixels that are not background pixels in either $im_{1t}$ or $im_2$.

The correlation metric is not absolute in the sense that there is no absolute best correlation that indicates that the two images are registered perfectly. The correlation is dependant on the distribution of the pixels; images with larger pixel values will produce a larger correlation. An absolute metric allows for a better sense of how well two images are registered to each other regardless of pixel distributions.

Instead of correlation, a mean-squared-difference (MSD) metric, defined in the following equation, can be used:

$$MSD = \frac{1}{N} \sum_{i,j,k} \sum (im_{1t}(i, j, k) - im_2(i, j, k))^2 \quad (10)$$

$$im_{1t}(i, j, k) \neq \text{background}$$

$$im_2(i, j, k) \neq \text{background}$$

where N is the number of pixels that are not background pixels in either $im_{1t}$ or $im_2$. With the MSD metric, perfectly registered images will produce a metric of zero.

The rigid-body transformation uses six parameters (tx,ty,tz,rx,ry,rz); translation in x, translation in y, translation in z, rotation about the x-axis, rotation about the y-axis, and rotation about the z-axis. The transformation is a mapping of a point v in 3-d space to a point v' in transformed space defined by the following equation:

$$v' = R_x R_y R_z v + \begin{bmatrix} t_x \\ t_y \\ t_z \end{bmatrix} \quad (11)$$

where $R_x$, $R_y$, and $R_z$ are the rotation matrices defined as:

$$R_x = \begin{bmatrix} 1 & 0 & 0 \\ 0 & \cos(r_x) & -\sin(r_x) \\ 0 & \sin(r_x) & \cos(r_x) \end{bmatrix} \quad (12)$$

$$R_y = \begin{bmatrix} \cos(r_y) & 0 & \sin(r_y) \\ 0 & 1 & 0 \\ -\sin(r_y) & 0 & \cos(r_y) \end{bmatrix} \quad (13)$$

$$R_z = \begin{bmatrix} \cos(r_z) & -\sin(r_z) & 0 \\ \sin(r_z) & \cos(r_z) & 0 \\ 0 & 0 & 1 \end{bmatrix}. \quad (14)$$

The first image is transformed so that it has the same bounding box as the second image. The transformation uses either linear interpolation or nearest-neighbor interpolation, and pixels that are transformed from outside the bounding box of the first image are set to the background value.

The initial rigid-body transformation parameters must be determined before a minimization search can be performed. The initial rotation parameters are all set to zero because only a small amount of rotation is expected between the two images. The initial translation parameters should be set so that the two nodules will overlap at the first iteration of the search procedure. Assuming that the nodules are in the center of the images, the initial translation parameters can be set to the difference between the centers of the two images, where the center of an image is defined as:

center$_x$=im.xlo+(im.xhi−im.xlo+1)/2 center$_y$=im.ylo+(im.yhi−im.ylo+1)/2 center$_z$=im.zlo+(im.zhi−im.zlo+1)/2

This assumption is not always true and a better method of determining the initial translation parameters is to use the centers of mass of the two nodules. Both images are thresholded at half of the largest pixel value in the image and the center of mass is calculated using the standard equations:

$$COM_x = \frac{\sum_{i,j,k} \sum \sum im(i, j, k) * i}{\sum \sum_{i,j,k} \sum im(i, j, k)}$$

$$COM_y = \frac{\sum_{i,j,k} \sum \sum im(i, j, k) * j}{\sum \sum_{i,j,k} \sum im(i, j, k)}$$

$$COM_z = \frac{\sum_{i,j,k} \sum \sum im(i, j, k) * k}{\sum \sum_{i,j,k} \sum im(i, j, k)}.$$

The initial translation parameter is equal to the difference between the centers of mass of the two images.

Using the registration metric, a function of six parameters, and the initial conditions, the registration problem is now converted into a minimization/maximization search problem. Specifically, given some initial condition, a minimum or maximum of the metric function is found by searching the 6-dimensional parameter space. The following subsections describe three different search methods: exhaustive search, hill-climbing, and Powell's method.

The exhaustive search is a brute force method that finds the minimum (or maximum) by calculating the metric for every possible set of parameters. Of course the number of possible parameters in a 6-dimensional search space is infinite. In order to reduce the search space, a limit of translation and rotation deviation from the initial condition, along with rotation and translation stepsizes, is imposed. Even with this search space reduction, the exhaustive search is still impractical.

Consider a case where translation is limited to 5 pixels in each direction and the rotation by 5 degrees in each direction. With stepsizes of 1 pixel of translation and 1 degree of rotation, the exhaustive search will perform $11^6$ or 1,771,561 metric evaluations. Suppose each metric evaluation takes 0.1 seconds, then the entire algorithm will take around 170,000 seconds, or 2,833 minutes, or just under two days. Even with such a seemingly small search space and appropriate stepsizes, the exhaustive search will take days to finish!

Hill-Climbing is a greedy search method. Starting at the initial condition and a set of translation and rotation stepsizes, the algorithm evaluates the metric for each of the possible 12 moves in parameter-space and then moves in the direction of the largest decrease (or increase). The algorithm terminates when there is no move that improves the metric.

By using a small step-size it is possible to calculate the best parameters up to some precision. Unfortunately, as the stepsize is decreased, the running-time of the algorithm increases because the algorithm must take smaller steps, and thus perform more metric evaluations to get to the minimum. One solution to this problem is to repeat the algorithm several times while using a decreasing stepsize. A detailed description of the complete hill-climbing algorithm is shown in FIG. 28.

Powell's method is a multi-dimensional direction-set search algorithm. Starting with an initial set of 6 directions and an initial condition, in each iteration the algorithm minimizes the metric by moving in each of the six directions. For a given direction, any line minimization technique could be used, however Brent's Method is chosen because it is a parabolic minimization technique that does not explicitly use derivatives. At the end of each iteration (one pass through each of the six directions), the oldest direction is replaced by the total direction moved during the current iteration. By doing this, the algorithm adapts itself to move along the most minimizing path. A more in depth description of Powell's method can be found in Chapter 10.5 in *Numerical Recipes in C*, W. Press, $2^{nd}$ Ed., Cambridge University Press, 1992, which is incorporated herein by reference.

Powell's method terminates when either all the parameters in one iteration change within some epsilon, or the metric after an iteration does not change by more than a tolerance value.

The registration algorithm works well on images with isolated nodules, but has trouble with images where the pleural surface is present because the pleural surface becomes the largest structure in the image. The largest structure has the largest effect on the metric value, causing the minimization technique to try to register the pleural surface to itself. Because the pleural wall can move and change shape with inspiration or position, there is no guarantee that the nodules near or along the pleural wall be registered correctly if the pleural wall is registered. A first method for addressing this problem is to use image masking or pixel masking. A mask is created that tells the algorithm to ignore the pleural surface and its contents will force the algorithm to register only the nodules together. A second method involves applying a function on the pixels so that all the pleural features become one intensity. This causes the registration algorithm to ignore structures like the ribs. A third method involves reducing the search space. A nodule-localization algorithm is used to find the centers of the nodules in both images. Taking the difference of the centers results in the translation parameters that overlap the nodules. Finally, the orientation of the nodules is determined by using the registration algorithm on only the rotation parameters.

The rigid-body registration algorithm is preferably implemented in the C programming language using the VisionX software library for the FreeBSD environment. The program, v3regrb, preferably inputs two input images of byte, short, or floating point pixel-types and a variety of options. The program preferably outputs the first input image registered to the second input image and a difference image associated with the two images. Both images preferably have the same bounding box as the second input image. The rigid-body transformation parameters for the registration are preferably stored with the metric and timing information with a history of the output images.

In order to increase the throughput of the registration process, the three-dimensional rigid-body transformation is preferably written into the program. The code for the transformation is preferably used from the existing stand-alone rigid-body transformation program (v3regrb). The rigid-body function preferably supports both linear and nearest-neighbor interpolation. The program may be modified to perform three-dimensional translation-only registration, two-dimensional rigid-body registration, and two-dimensional translation-only registration.

E. Removal of the Pleural Surface from Juxtapleural Nodules in Thresholded High-Resolution CT Images The algorithm takes a binary (thresholded) image as its input. The algorithm also requires the location of a point near the center of the nodule. If the image is some region-of-interest that has been generated by a radiologist, then it is assumed that the nodule is in the center of the image. In this case the initial starting point will be the center of the image. The pleural-surface removal algorithm is shown in FIG. 29.

The pleural surface removal algorithm works by iteratively moving a plane towards the pleural-surface. The algorithm starts with an initial point P' inside the nodule and a direction towards the wall, d'. The direction is calculated by taking the difference between the center of mass of a spherical region centered on P' and the starting location P'.

Figure 30A:
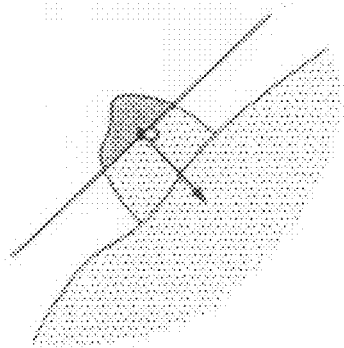
FIG. 30 illustrates an example of the pleural wall removal algorithm: The cut nodule is shown as dark gray white the rest of the nodule and the pleural surface are shown in light gray. (A) Given the initial location and direction, (B) the plane is moved in the direction. (C) The plane eventually intersects the pleural wall causing an increase in the size change of the cut nodule, and (D) the plane is reorientated to minimize the size of the cut nodule. At the next iteration, (E) the plane intersects the pleural wall, but this time (F) reorientating the plane to minimize the cut nodule still results in a large increase in size change. The algorithm terminates, returning the cut nodule from the previous iteration, (D)
Figure 30B:
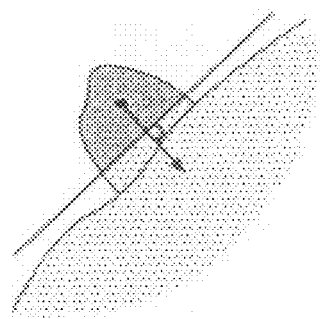

With each iteration, a new location $P_i$ is calculated by stepping in direction d from the previous location $P_{i-1}$. Plane A, normal to direction d and passing through point P, separates the nodule from the pleural surface. This cut nodule is the connected component region that contains point P and that is behind the plane A. As the plane moves towards the pleural wall, the size of the cut nodule increases. FIGS. 30A and 30B show the cut nodule for two iterations.

Figure 30C:
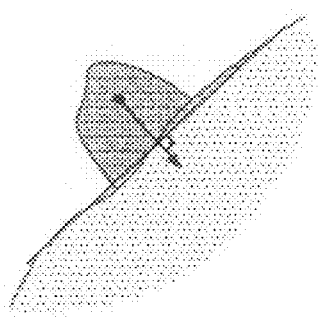
Figure 30D:
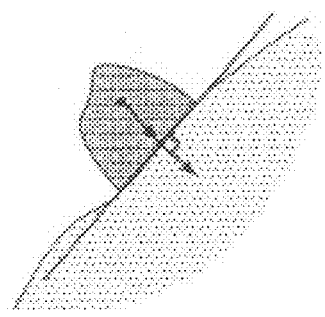
Figure 30E:
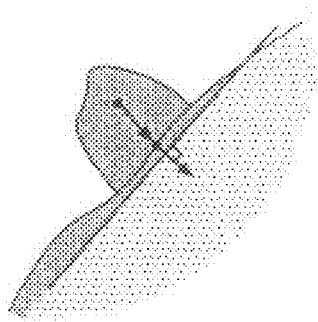
Figure 30F:
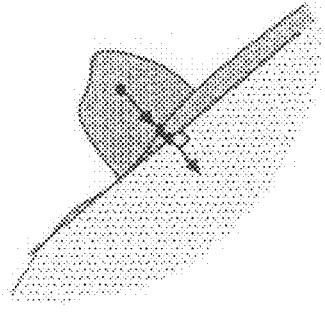

The algorithm keeps track of the difference Δ in the size of the cut nodule between iterations. When the plane intersects the pleural surface, as seen in FIG. 30C, the difference Δ increases dramatically. This condition is manifested by the change in the difference increasing by more than $\gamma_{max}$. When this occurs, the size of the cut nodule is minimized by reorientating the plane by changing the direction d while keeping the point P fixed, as in FIG. 30D. Additionally, the size difference and change in difference are recalculated. If the change in difference is less than $\gamma_{max}$, then the algorithm keeps iterating. Otherwise, the algorithm terminates and returns the cut nodule formed by using the plane in the previous iteration.

FIG. 30 shows a two-dimensional example of the algorithm. The cut nodule is shown as dark gray while the rest of the nodule and the pleural surface are light gray. The initial starting point and the initial direction are shown in FIG. 30A. FIG. 30B shows an iteration where the plane does not intersect the pleural wall. FIG. 30C shows an iteration where the plane intersects the pleural surface, causing the change in the nodule size to increase. In FIG. 30D the plane is reorientated to minimize the cut nodule, forming a new direction. After another iteration, FIG. 30E shows the plane intersects the pleural wall again, but reorientating the plane still leads to a large increase in nodule size, as seen in FIG. 30F. Thus, the algorithm terminates and returns the cut nodule from the previous iteration, FIG. 30D.

In this section, a specific implementation of the algorithm is discussed. A seeded region growing algorithm is used to find the cut-nodule region, and a hill-climbing search is used to perform the minimization when reorientating the plane. This section first discusses the equations used for the plane, followed by a description of the region growing and hill-climbing algorithms.

The representation of the plane has four parameters and is defined as:

$$ax+by+cz+d=0 \qquad (15)$$

Given a direction normal to the plane, v, and a point on the plane, P, the parameters of the plane are calculated as:

$$a=v_x \qquad (16)$$

$$b=v_y \qquad (17)$$

$$c=v_z \qquad (18)$$

$$d=-(aP_x+bP_y+cP_z) \qquad (19)$$

Finally, a point p is behind the plane if:

$$ap_x+bp_y+cp_z+d<0 \qquad (20)$$

A recursive region growing is used to determine the cut-nodule region. The starting point of the region-growing algorithm is the initial starting location P', and the plane A is calculated from $P_i$ and $d_i$. A description of the region growing algorithm is shown in FIG. 31. For the given pixel p, the algorithm marks it as visited and then determines if it is behind the plane A. If it is not, then the algorithm exits. Otherwise, the pixel p is marked as part of the cut-nodule region, and the algorithm is recursively called for each of the six possible 1-pixel moves from p if the new point has not been visited yet and it is also a foreground pixel.

A simple greedy search algorithm is used to reorientate the plane so that it minimizes the cut-nodule size. A new plane is calculated by changing the direction normal to the plane. The hill-climbing algorithm is shown in FIG. 32. The hill-climbing algorithm takes the initial direction and a small stepsize. Next, the size of the cut-nodule is calculated for the planes formed by moving the direction in the six possible coordinate directions. If a smaller size is calculated, then the direction is moved in the direction of the largest decrease. The new direction is normalized to one, and the algorithm is repeated. If there is no decrease in the cut-nodule size, then the algorithm terminates.

The algorithm is preferably implemented in the C programming language for the VisionX software package on a FreeBSD UNIX system. The program preferably operates on binary images that have floating point, byte, or short pixel types. The program preferably outputs the segmented nodule and two debugging images. The initial conditions, initial direction, and termination criteria are preferably specified by options.

Thus, while there have been described what are presently believed to be the preferred embodiments of the invention, those skilled in the art will realize that changes and modifications may be made thereto without departing from the spirit of the invention, and is intended to claim all such changes and modifications as fall within the true scope of the invention.

What is claimed is:

1. A method for finding the location, P', and size, r', of a pulmonary nodule in a high-resolution three-dimensional computed tomography (CT) image, the method comprising:
    (a) selecting a set of initial processing parameters including an initial location, $P_1$, an initial size, $r_1$, and target value, T;
    (b) computing an initial new location $P_i$ of the nodule with a three-dimensional density-based locator template function in a first computer process performed by a computing device;
    (c) incrementally increasing size, $r_i$ in a second computer process performed by a computing device;
    (d) computing a new location $P_i$ of the nodule with the three-dimensional density-based locator template function in a third computer process performed by a computing device;
    (e) computing a size metric with a three-dimensional density-based sizing template function in a fourth computer process performed by a computing device;
    (f) repeating steps (c) through (e) until the size metric is less than the target value;
    (g) returning the location, P', and the size, r', from the previous iteration of steps (c) through (e) in a fifth computer process performed by a computing device.

2. A method for finding the location, P, and size, r, of a pulmonary nodule in a high-resolution three-dimensional computed tomography image, the method comprising:
    (a) windowing the image to ignore bone structures in a first computer process performed by a computing device;
    (b) selecting a three-dimensional density-based locator template function and a three-dimensional density-based sizing template function in a second computer process performed by a computing device;
    (c) selecting a set of initial processing parameters including: an initial location, P; size, r; and termination criteria;
    (d) performing a search to determine a maximum response of the three-dimensional density-based locator template function in a third computer process performed by a computing device;
    (e) determining a response of the three-dimensional density-based sizing template function and comparing the response to the termination criteria in a fourth computer process performed by a computing device;
    (f) incrementally increasing the size, r, only if the termination criteria has not been satisfied and repeating steps (d) and (e) in a fifth computer process performed by a computing device; and
    (g) outputting the location, P, and size, r, of the nodule in a sixth computer process performed by a computing device.

3. A method for finding the location and size of a pulmonary nodule as defined in claim 2, wherein the windowing comprises clipping the image at intensities over about 1000.

4. A method for finding the location and size of a pulmonary nodule as defined in claim 2, wherein the three-dimensional density-based locator template function is a Gaussian template function.

5. A method for finding the location and size of a pulmonary nodule as defined in claim 2, wherein the three-dimensional density-based locator template function is a Laplacian of the Gaussian template function.

6. A method for finding the location and size of a pulmonary nodule as defined in claim 2, wherein the three-dimensional density-based locator template function is a difference of Gaussians template function.

7. A method for finding the location and size of a pulmonary nodule as defined in claim 2, wherein each of the three-dimensional density-based template functions has at least four parameters corresponding to the x-location, y-location, z-location, and radius.

8. A method for finding the location and size of a pulmonary nodule as defined in claim 2, wherein the initial location, P, is calculated from the image.

9. A method for finding the location and size of a pulmonary nodule as defined in claim 2, wherein the initial location, P, is specified by a user.

10. A method for finding the location and size of a pulmonary nodule as defined in claim 2, wherein the search is performed by a hill climbing method.

11. A method for finding the location and size of a pulmonary nodule as defined in claim 2, wherein the search is performed by Powell's method.

12. A pulmonary nodule finding apparatus for finding the location, P', and size, r', of a pulmonary nodule in a high-resolution computed tomography (CT) image, the pulmonary nodule finding apparatus comprising:
    a computing device to:
    (a) select a set of initial processing parameters including an initial location, $P_1$, an initial size, $r_1$, and target value, T;
    (b) compute an initial new location $P_i$ of the nodule with a three-dimensional density-based locator template function;
    (c) incrementally increase size, $r_i$;
    (d) compute a new location $P_i$ of the nodule with the three-dimensional density-based locator template function;
    (e) compute a size metric with a three-dimensional density-based sizing template function;

(f) repeat steps (c) through (e) until the size metric is less than the target value;
(g) return the location, P', and the size, r', from the previous iteration of steps (c) through (e).

13. A pulmonary nodule finding apparatus for finding the location, P, and size, r, of a pulmonary nodule in a high-resolution computed tomography image, the pulmonary nodule finding apparatus comprising:
a computing device to:
(a) window the image to ignore bone structures;
(b) select a three-dimensional density-based locator template function and a three-dimensional density-based sizing template function;
(c) select a set of initial processing parameters including: an initial location, P; size, r; and termination criteria;
(d) perform a search to determine a maximum response of the three-dimensional density-based locator template function;
(e) determine a response of the three-dimensional density-based sizing template function and compare the response to the termination criteria;
(f) incrementally increase the size, r, only if the termination criteria has not been satisfied and repeating steps (d) and (e); and
(g) output the location, P, and size, r, of the nodule.

14. A pulmonary nodule finding apparatus as defined in claim 13, wherein the image is clipped at intensities over about 1000 to window the image.

15. A pulmonary nodule finding apparatus as defined in claim 13, wherein the three-dimensional density-based locator template function is a Gaussian template function.

16. A pulmonary nodule finding apparatus as defined in claim 13, wherein the three-dimensional density-based locator template function is a Laplacian of the Gaussian template function.

17. A pulmonary nodule finding apparatus as defined in claim 13, wherein the three-dimensional density-based locator template function is a difference of Gaussians template function.

18. A pulmonary nodule finding apparatus as defined in claim 13, wherein each of the three-dimensional density-based template functions has at least four parameters corresponding to the x-location, y-location, z-location, and radius.

19. A pulmonary nodule finding apparatus as defined in claim 13, wherein the initial location, P, is calculated from the image.

20. A pulmonary nodule finding apparatus as defined in claim 13, wherein the initial location, P, is specified by a user.

21. A pulmonary nodule finding apparatus as defined in claim 13, wherein the search is performed by a hill climbing method.

22. A pulmonary nodule finding apparatus as defined in claim 13, wherein the search is performed by Powell's method.

23. An article of manufacture for finding the location, P', and size, r', of a pulmonary nodule in a high-resolution computed tomography (CT) image, the article comprising:
a tangible computer readable medium including one or more computer instructions thereon which when executed by a computing device implement the steps of:
(a) selecting a set of initial processing parameters including an initial location, $P_1$, an initial size, $r_1$, and target value, T;
(b) computing an initial new location $P_i$ of the nodule with a three-dimensional density-based locator template function;
(c) incrementally increasing size, $r_i$;
(d) computing a new location $P_i$ of the nodule with the three-dimensional density-based locator template function;
(e) computing a size metric with a three-dimensional density-based sizing template function;
(f) repeating steps (c) through (e) until the size metric is less than the target value;
(g) returning the location, P', and the size, r', from the previous iteration of steps (c) through (e).

24. An article of manufacture for finding the location, P, and size, r, of a pulmonary nodule in a high-resolution computed tomography image, the article comprising:
a tangible computer readable medium including one or more computer instructions thereon which when executed by a computing device implement the steps of:
(a) windowing the image to ignore bone structures;
(b) selecting a three-dimensional density-based locator template function and a three-dimensional density-based sizing template function;
(c) selecting a set of initial processing parameters including: an initial location, P; size, r; and termination criteria;
(d) performing a search to determine a maximum response of the three-dimensional density-based locator template function;
(e) determining a response of the three-dimensional density-based sizing template function and comparing the response to the termination criteria;
(f) incrementally increasing the size, r, only if the termination criteria has not been satisfied and repeating steps (d) and (e); and
(g) outputting the location, P, and size, r, of the nodule.

25. An article of manufacture for finding the location and size of a pulmonary nodule as defined in claim 24, wherein the windowing comprises clipping the image at intensities over about 1000.

26. An article of manufacture for finding the location and size of a pulmonary nodule as defined in claim 24, wherein the three-dimensional density-based locator template function is a Gaussian template function.

27. An article of manufacture for finding the location and size of a pulmonary nodule as defined in claim 24, wherein the three-dimensional density-based locator template function is a Laplacian of the Gaussian template function.

28. An article of manufacture for finding the location and size of a pulmonary nodule as defined in claim 24, wherein the three-dimensional density-based locator template function is a difference of Gaussians template function.

29. An article of manufacture for finding the location and size of a pulmonary nodule as defined in claim 24, wherein each of the three-dimensional density-based template functions has at least four parameters corresponding to the x-location, y-location, z-location, and radius.

30. An article of manufacture for finding the location and size of a pulmonary nodule as defined in claim 24, wherein the initial location, P, is calculated from the image.

31. An article of manufacture for finding the location and size of a pulmonary nodule as defined in claim 24, wherein the initial location, P, is specified by a user.

32. An article of manufacture for finding the location and size of a pulmonary nodule as defined in claim 24, wherein the search is performed by a hill climbing method.

33. An article of manufacture finding the location and size of a pulmonary nodule as defined in claim 24, wherein the search is performed by Powell's method.

* * * * *

UNITED STATES PATENT AND TRADEMARK OFFICE
CERTIFICATE OF CORRECTION

PATENT NO. : 7,660,451 B2 Page 1 of 1
APPLICATION NO. : 12/074211
DATED : February 9, 2010
INVENTOR(S) : Reeves et al.

It is certified that error appears in the above-identified patent and that said Letters Patent is hereby corrected as shown below:

IN THE PATENT:

Column 8, line 47:

Now reads: "to the current mass mass."

Should read: -- to the current mass $mass_i$. --

Column 9, line 12:

Now reads: "the current mass mass,"

Should read: -- the current mass $mass_i$, --

Column 20, line 64:

Now reads: "3 or 5 times the radius α"

Should read: -- 3 or 5 times the radius σ --

Signed and Sealed this

Twelfth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,660,451 B2
APPLICATION NO. : 12/074211
DATED : February 9, 2010
INVENTOR(S) : Reeves et al.

It is certified that error appears in the above-identified patent and that said Letters Patent is hereby corrected as shown below:

IN THE PATENT:

Column 8, line 39:

Now reads: "from the current mass mass."

Should read: -- from the current mass $mass_i$. --

Signed and Sealed this

Twenty-first Day of December, 2010

David J. Kappos
*Director of the United States Patent and Trademark Office*